(12) United States Patent
Kochenderfer

(10) Patent No.: US 11,236,161 B2
(45) Date of Patent: *Feb. 1, 2022

(54) CHIMERIC ANTIGEN RECEPTORS TARGETING CD-19

(71) Applicant: The United States of America, as represented by the Secretary, Department of Health and Human Services, Bethesda, MD (US)

(72) Inventor: James N. Kochenderfer, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 144 days.

This patent is subject to a terminal disclaimer.

(21) Appl. No.: 16/360,281

(22) Filed: Mar. 21, 2019

(65) Prior Publication Data

US 2019/0202913 A1    Jul. 4, 2019

Related U.S. Application Data

(63) Continuation of application No. 15/315,533, filed as application No. PCT/US2015/033473 on Jun. 1, 2015, now Pat. No. 10,287,350.

(60) Provisional application No. 62/006,313, filed on Jun. 2, 2014.

(51) Int. Cl.
| | |
|---|---|
| A61K 35/17 | (2015.01) |
| C07K 14/705 | (2006.01) |
| C07K 16/28 | (2006.01) |
| C07K 14/725 | (2006.01) |
| C07K 14/735 | (2006.01) |
| C07K 16/30 | (2006.01) |
| C12N 5/0783 | (2010.01) |

(52) U.S. Cl.
CPC .......... *C07K 16/2803* (2013.01); *A61K 35/17* (2013.01); *C07K 14/705* (2013.01); *C07K 14/7051* (2013.01); *C07K 14/70517* (2013.01); *C07K 14/70521* (2013.01); *C07K 14/70535* (2013.01); *C07K 14/70578* (2013.01); *C07K 16/3061* (2013.01); *C12N 5/0636* (2013.01); *C07K 2317/21* (2013.01); *C07K 2317/622* (2013.01); *C07K 2317/70* (2013.01); *C07K 2319/00* (2013.01); *C07K 2319/02* (2013.01); *C07K 2319/03* (2013.01); *C07K 2319/33* (2013.01); *C07K 2319/74* (2013.01); *C12N 2510/00* (2013.01)

(58) Field of Classification Search
CPC .. A61K 35/17; C07K 14/705; C07K 16/3061; C07K 2317/21; C07K 2317/22; C07K 2317/70; C07K 2319/00; C07K 2319/03; C07K 2319/33; C07K 2319/74; C12N 5/0636; C12N 5/0646; C12N 2510/00
See application file for complete search history.

(56) References Cited

U.S. PATENT DOCUMENTS

| | | | |
|---|---|---|---|
| 7,741,465 | B1 | 6/2010 | Eshhar et al. |
| 8,211,422 | B2 | 7/2012 | Eshhar et al. |
| 10,287,350 | B2 * | 5/2019 | Kochenderfer .... C07K 16/2803 |
| 2010/0104509 | A1 | 4/2010 | King et al. |
| 2012/0093842 | A1 | 4/2012 | Esshar et al. |
| 2012/0213783 | A1 | 8/2012 | Rosenberg et al. |
| 2013/0266551 | A1 | 10/2013 | Campana et al. |
| 2014/0271635 | A1 * | 9/2014 | Brogdon .......... C07K 14/70578 424/133.1 |
| 2015/0038684 | A1 | 2/2015 | Jensen | |

FOREIGN PATENT DOCUMENTS

| | | |
|---|---|---|
| JP | 2010-513303 A | 4/2010 |
| WO | WO 97/15669 A1 | 5/1997 |
| WO | WO 2009/054863 A2 | 4/2009 |
| WO | WO 2009/091826 A2 | 7/2009 |
| WO | WO 2012/079000 A1 | 6/2012 |
| WO | WO 2012/138475 A1 | 10/2012 |
| WO | WO 2013/123061 A1 | 8/2013 |
| WO | WO 2013/154760 A1 | 10/2013 |
| WO | WO 2014/153270 A1 | 9/2014 |

OTHER PUBLICATIONS

Sadelain et al, Cancer Discovery 3(4):388-398, available online Apr. 2, 2013.*
UniprotKB—P01732 (CD8A_HUMAN). (12 pages) Jul. 21, 1986.
Littman, et al., "The Isolation and Sequence of the Gene Encoding T8: A Molecule Defining Functional Classes of T Lymphocytes," *Cell*, 40: 237-246 (1985).
Tammana et al., "4-1BB and CD28 Signaling Plays a Synergistic Role in Redirecting Umbilical Cord Blood T Cells Against B-Cell Malignancies," *Human Gene Therapy*, 21: 75-86(2010).
Genbank Accession No. ADM64594.1, published Jun. 11, 2012.
Ling et al., "Advances in cancer immunotherapy based on chimeric antigen receptor," *Translational Med. J.*, 4 (3), 97-104 (2015).
Alabanza et al., "Function of Novel Anti-CD19 Chimeric Antigen Receptors with Human Variable Regions is Affected by Hinge and Transmembrane Domains," *Mol. Ther.*, 25 (11), 2452-2465 (Epub Jul. 27, 2017).
Beatty, Haas and Maus et al., "Mesothelin-specific chimeric antigen receptor mRNA-engineered T cells induce anti-tumor activity in solid malignancies," *Cancer Immunology Research*, 2 (2), 112-120 (2014).

(Continued)

*Primary Examiner* — Kevin K Hill
(74) *Attorney, Agent, or Firm* — Leydig, Voit & Mayer, Ltd.

(57) ABSTRACT

The invention is directed to a chimeric antigen receptor (CAR) directed against CD19, which comprises an amino acid sequence of any one of SEQ ID NO: 1-SEQ ID NO: 13. The invention also provides T-cells expressing the CAR and methods for destroying malignant B-cells.

20 Claims, 10 Drawing Sheets

Specification includes a Sequence Listing.

(56) References Cited

OTHER PUBLICATIONS

Brentjens et al., "CD19-targeted T cells rapidly induce molecular remissions in adults with chemotherapy-refractory acute lymphoblastic leukemia," *Science Translational Medicine*, 5 (177), 177ra38 (2013), 19 pages, Author Manuscript.
Brentjens et al., "Eradication of systemic B-cell tumors by genetically targeted human T lymphocytes co-stimulated by CD80 and interleukin-15," *Nature Medicine*, 9 (3), 279-286 (2003).
Brentjens et al., "Genetically targeted T cells eradicate systemic acute lymphoblastic leukemia xenografts," *Clinical Cancer Research*, 13 (18), 5426-5435 (2007).
Brentjens et al., "Novel cellular therapies for leukemia: CAR-modified T cells targeted to the CD19 antigen," *Hematology. American Society of Hematology. Education Program*, 2012, 143-151 (2012).
Brentjens et al., "Safety and persistence of adoptively transferred autologous CD19-targeted T cells in patients with relapsed or chemotherapy refractory B-cell leukemias," *Blood*, 118 (18), 4817-4828 (2011).
Brudno et al., "Clinical anti-lymphoma activity and toxicity of T cells expressing a novel anti-CD19 chimeric antigen receptor with fully-human variable regions," *ASCO Meeting Library*, abstract cited in J Clin Oncol., 36, 2018 (suppl; abstr 3052).
Burns et al., "Vesicular stomatitis virus G glycoprotein pseudotyped retroviral vectors: concentration to very high titer and efficient gene transfer into mammalian and nonmammalian cells," *Proc. Natl. Acad. Sci., USA*, 90 (17), 8033-8037 (1993).
Cheadle et al., "Natural expression of the CD19 antigen impacts the long-term engraftment but not antitumor activity of CD19-specific engineered T cells," *Journal of Immunology*, 184 (4), 1885-1896 (2010).
Cooper et al., "T-cell clones can be rendered specific for CD19: toward the selective augmentation of the graft-versus-B-lineage leukemia effect," *Blood*, 101 (4), 1637-1644 (2003).
Grupp et al., "Chimeric antigen receptor-modified T cells for acute lymphoid leukemia," *New England Journal of Medicine*, 368 (16), 1509-1518 (2013).
Hermans et al., "The VITAL assay: a versatile fluorometric technique for assessing CTL- and NKT-mediated cytotoxicity against multiple targets in vitro and in vivo," *Journal of Immunological Methods*, 285 (1), 25-40 (2004).
Hombach et al., "Costimulation by chimeric antigen receptors revisited the T cell antitumor response benefits from combined CD28-OX40 signalling," *International Journal of Cancer*, 129 (12), 2935-2944 (2011).
Jensen et al., "Antitransgene rejection responses contribute to attenuated persistence of adoptively transferred CD20/CD19-specific chimeric antigen receptor redirected T cells in humans," *Biology of Blood and Marrow Transplantation*, 16 (9), 1245-1256 (2010).
Kalos et al., "T cells with chimeric antigen receptors have potent antitumor effects and can establish memory in patients with advanced leukemia," *Science Translational Medicine*, 3 (95), 95ra73 (2011), 21 pages, Author Manuscript.
Kochenderfer et al., "Adoptive transfer of syngeneic T cells transduced with a chimeric antigen receptor that recognizes murine CD19 can eradicate lymphoma and normal B cells," *Blood*, 116 (19), 3875-3886 (2010).
Kochenderfer et al., "B-cell depletion and remissions of malignancy along with cytokine-associated toxicity in a clinical trial of anti-CD19 chimeric-antigen-receptor-transduced T cells," *Blood*, 119 (12), 2709-2720 (2012).
Kochenderfer et al., "Construction and preclinical evaluation of an anti-CD19 chimeric antigen receptor," *Journal of Immunotherapy*, 32 (7), 689-702 (2009), Author Manuscript.
Kochenderfer et al., "Eradication of B-lineage cells and regression of lymphoma in a patient treated with autologous T cells genetically engineered to recognize CD19," *Blood*, 116 (20), 4099-4102 (2010).
Kochenderfer et al., "Treating B-cell cancer with T cells expressing anti-CD19 chimeric antigen receptors," *Nature Reviews. Clinical Oncology*, 10 (5), 267-276 (2013).
Lamers et al., "Immune responses to transgene and retroviral vector in patients treated with ex vivo-engineered T cells," *Blood*, 117 (1), 72-82 (2011).
Latza et al., "The human OX40 homolog: cDNA structure, expression and chromosomal assignment of the ACT35 antigen," *European Journal of Immunology*, 24 (3), 677-683 (1994).
Mannering et al., "A sensitive method for detecting proliferation of rare autoantigen-specific human T cells," *Journal of Immunological Methods*, 283 (1-2), 173-183 (2003).
Moran et al., "The TNFRs OX40, 4-1BB, and CD40 as targets for cancer immunotherapy," *Current Opinion in Immunology*, 25 (2), 230-237 (2013).
Nadler et al., "B4, a human B lymphocyte-associated antigen expressed on normal, mitogen-activated, and malignant B lymphocytes," *Journal of Immunology*, 131 (1), 244-250 (1983).
Nicholson et al., "Construction and characterisation of a functional CD19 specific single chain Fv fragment for immunotherapy of B lineage leukaemia and lymphoma," *Molecular Immunology*, 34 (16-17), 1157-1165 (1997).
Ochi et al., "Functional immunoglobulin M production after transfection of cloned immunoglobulin heavy and light chain genes into lymphoid cells," *Proceedings of the National Academy of Sciences of the United States of America*, 80 (20), 6351-6355 (1983).
Porter et al., "Chimeric antigen receptor-modified T cells in chronic lymphoid leukemia," *New England Journal of Medicine*, 365 (8), 725-733 (2011).
Porter et al., "Comparison of efficiency of infection of human gene therapy target cells via four different retroviral receptors," *Human Gene Therapy*, 7 (8), 913-919 (1996).
Rubio et al., "Ex vivo identification, isolation and analysis of tumor-cytolytic T cells," *Nature Medicine*, 9 (11), 1377-1382 (2003).
Sadelain, M. et al., "The Basic Principles of Chimeric Antigen Receptor Design," *Cancer Discovery*, 3(4): 388-398 (2013).
Savoldo et al., "CD28 costimulation improves expansion and persistence of chimeric antigen receptor-modified T cells in lymphoma patients," *Journal of Clinical Investigation*, 121 (5), 1822-1826 (2011).
Weinberg et al., "Science gone translational: the OX40 agonist story," *Immunological Reviews*, 244 (1), 218-231 (2011), Author Manuscript.
Yang et al., "A simplified method for the clinical-scale generation of central memory-like CD8+ T cells after transduction with lentiviral vectors encoding antitumor antigen T-cell receptors," *Journal of Immunotherapy*, 33 (6), 648-658 (2010).
U.S. Appl. No. 15/315,533, filed Dec. 1, 2016.

* cited by examiner

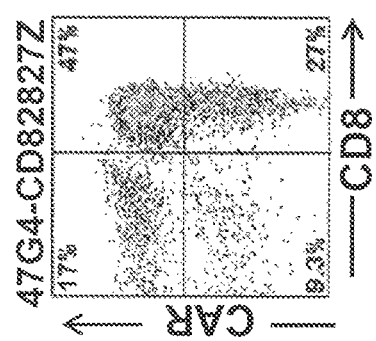
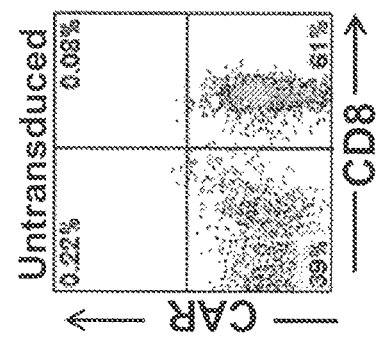
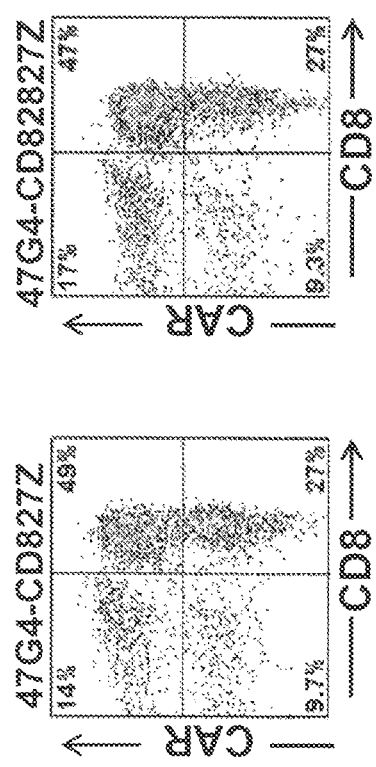
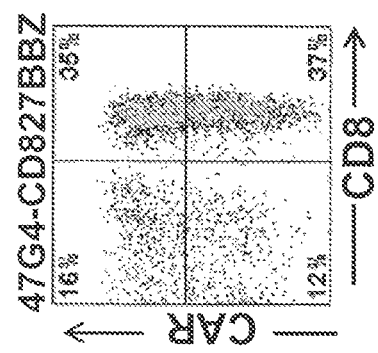

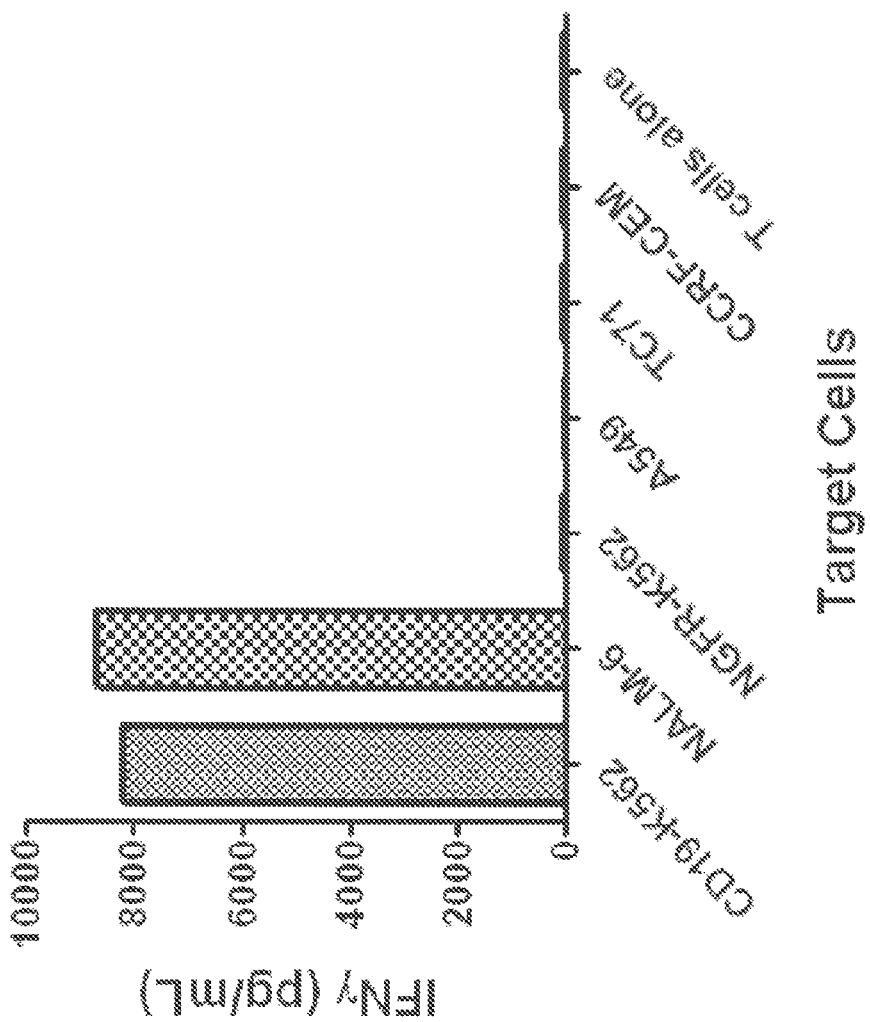

47G4-CD827Z

47G4-CD82827Z

47G4-CD827BBZ

Untransduced

SEQUENCE LISTING

<160> NUMBER OF SEQ ID NOS: 15

<210> SEQ ID NO 1
<211> LENGTH: 502
<212> TYPE: PRT
<213> ORGANISM: Artificial Sequence
<220> FEATURE:
<223> OTHER INFORMATION: Synthetic

<400> SEQUENCE: 1

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Thr Leu
            20                  25                  30

Ser Leu Ser Pro Gly Glu Arg Ala Thr Leu Ser Cys Arg Ala Ser Gln
        35                  40                  45

Ser Val Ser Ser Ser Tyr Leu Ala Trp Tyr Gln Gln Lys Pro Gly Gln
    50                  55                  60

Ala Pro Arg Leu Leu Ile Tyr Gly Ala Ser Ser Arg Ala Thr Gly Ile
65                  70                  75                  80
```

```
Pro Asp Arg Phe Ser Gly Ser Gly Ser Gly Thr Asp Phe Thr Leu Thr
                85                  90                  95
Ile Ser Arg Leu Glu Pro Glu Asp Phe Ala Val Tyr Tyr Cys Gln Gln
            100                 105                 110
Tyr Gly Ser Ser Arg Phe Thr Phe Gly Pro Gly Thr Lys Val Asp Ile
        115                 120                 125
Lys Gly Ser Thr Ser Gly Ser Gly Lys Pro Gly Ser Gly Glu Gly Ser
130                 135                 140
Thr Lys Gly Gln Val Gln Leu Val Gln Ser Ala Glu Val Lys Lys
145                 150                 155                 160
Pro Gly Ser Ser Val Lys Val Ser Cys Lys Asp Ser Gly Gly Thr Phe
                165                 170                 175
Ser Ser Tyr Ala Ile Ser Trp Val Arg Gln Ala Pro Gly Gln Gly Leu
            180                 185                 190
Glu Trp Met Gly Gly Ile Ile Pro Ile Phe Gly Thr Thr Asn Tyr Ala
        195                 200                 205
Gln Gln Phe Gln Gly Arg Val Thr Ile Thr Ala Asp Glu Ser Thr Ser
    210                 215                 220
Thr Ala Tyr Met Glu Leu Ser Ser Leu Arg Ser Glu Asp Thr Ala Val
225                 230                 235                 240
Tyr Tyr Cys Ala Arg Glu Ala Val Ala Ala Asp Trp Leu Asp Pro Trp
                245                 250                 255
Gly Gln Gly Thr Leu Val Thr Val Ser Ser Phe Val Pro Val Phe Leu
            260                 265                 270
Pro Ala Lys Pro Thr Thr Thr Pro Ala Pro Arg Pro Pro Thr Pro Ala
        275                 280                 285
Pro Thr Ile Ala Ser Gln Pro Leu Ser Leu Arg Pro Glu Ala Cys Arg
    290                 295                 300
Pro Ala Ala Gly Gly Ala Val His Thr Arg Gly Leu Asp Phe Ala Cys
305                 310                 315                 320
Asp Ile Tyr Ile Trp Ala Pro Leu Ala Gly Thr Cys Gly Val Leu Leu
                325                 330                 335
Leu Ser Leu Val Ile Thr Leu Tyr Cys Asn His Arg Asn Arg Ser Lys
            340                 345                 350
Arg Ser Arg Leu Leu His Ser Asp Tyr Met Asn Met Thr Pro Arg Arg
        355                 360                 365
Pro Gly Pro Thr Arg Lys His Tyr Gln Pro Tyr Ala Pro Pro Arg Asp
    370                 375                 380
Phe Ala Ala Tyr Arg Ser Arg Val Lys Phe Ser Arg Ser Ala Asp Ala
385                 390                 395                 400
Pro Ala Tyr Gln Gln Gly Gln Asn Gln Leu Tyr Asn Glu Leu Asn Leu
                405                 410                 415
Gly Arg Arg Glu Glu Tyr Asp Val Leu Asp Lys Arg Arg Gly Arg Asp
            420                 425                 430
Pro Glu Met Gly Gly Lys Pro Arg Arg Lys Asn Pro Gln Glu Gly Leu
        435                 440                 445
Tyr Asn Glu Leu Gln Lys Asp Lys Met Ala Glu Ala Tyr Ser Glu Ile
    450                 455                 460
Gly Met Lys Gly Glu Arg Arg Arg Gly Lys Gly His Asp Gly Leu Tyr
465                 470                 475                 480
Gln Gly Leu Ser Thr Ala Thr Lys Asp Thr Tyr Asp Ala Leu His Met
                485                 490                 495
Gln Ala Leu Pro Pro Arg
```

500

<210> SEQ ID NO 2
<211> LENGTH: 508
<212> TYPE: PRT
<213> ORGANISM: Artificial Sequence
<220> FEATURE:
<223> OTHER INFORMATION: Synthetic

<400> SEQUENCE: 2

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Thr Leu
            20                  25                  30

Ser Leu Ser Pro Gly Glu Arg Ala Thr Leu Ser Cys Arg Ala Ser Gln
        35                  40                  45

Ser Val Ser Ser Ser Tyr Leu Ala Trp Tyr Gln Gln Lys Pro Gly Gln
    50                  55                  60

Ala Pro Arg Leu Leu Ile Tyr Gly Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
            100                 105                 110

Tyr Gly Ser Ser Arg Phe Thr Phe Gly Pro Gly Thr Lys Val Asp Ile
        115                 120                 125

Lys Gly Ser Thr Ser Gly Ser Gly Lys Pro Gly Ser Gly Glu Gly Ser
    130                 135                 140

Thr Lys Gly Gln Val Gln Leu Val Gln Ser Gly Ala Glu Val Lys Lys
145                 150                 155                 160

Pro Gly Ser Ser Val Lys Val Ser Cys Lys Asp Ser Gly Gly Thr Phe
                165                 170                 175

Ser Ser Tyr Ala Ile Ser Trp Val Arg Gln Ala Pro Gly Gln Gly Leu
            180                 185                 190

Glu Trp Met Gly Gly Ile Ile Pro Ile Phe Gly Thr Thr Asn Tyr Ala
        195                 200                 205

Gln Gln Phe Gln Gly Arg Val Thr Ile Thr Ala Asp Glu Ser Thr Ser
    210                 215                 220

Thr Ala Tyr Met Glu Leu Ser Ser Leu Arg Ser Glu Asp Thr Ala Val
225                 230                 235                 240

Tyr Tyr Cys Ala Arg Glu Ala Val Ala Ala Asp Trp Leu Asp Pro Trp
                245                 250                 255

Gly Gln Gly Thr Leu Val Thr Val Ser Ser Phe Val Pro Val Phe Leu
            260                 265                 270

Pro Ala Lys Pro Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Asn His Arg Asn Arg Phe Ser
            340                 345                 350

Val Val Lys Arg Gly Arg Lys Lys Leu Leu Tyr Ile Phe Lys Gln Pro
```

```
                355                 360                 365
Phe Met Arg Pro Val Gln Thr Thr Gln Glu Glu Asp Gly Cys Ser Cys
    370                 375                 380

Arg Phe Pro Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 3
<211> LENGTH: 509
<212> TYPE: PRT
<213> ORGANISM: Artificial Sequence
<220> FEATURE:
<223> OTHER INFORMATION: Synthetic

<400> SEQUENCE: 3

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Thr Leu
                20                  25                  30

Ser Leu Ser Pro Gly Glu Arg Ala Thr Leu Ser Cys Arg Ala Ser Gln
            35                  40                  45

Ser Val Ser Ser Ser Tyr Leu Ala Trp Tyr Gln Gln Lys Pro Gly Gln
    50                  55                  60

Ala Pro Arg Leu Leu Ile Tyr Gly Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
            100                 105                 110

Tyr Gly Ser Ser Arg Phe Thr Phe Gly Pro Gly Thr Lys Val Asp Ile
        115                 120                 125

Lys Gly Ser Thr Ser Gly Ser Gly Lys Pro Gly Ser Gly Glu Gly Ser
    130                 135                 140

Thr Lys Gly Gln Val Gln Leu Val Gln Ser Gly Ala Glu Val Lys Lys
145                 150                 155                 160

Pro Gly Ser Ser Val Lys Val Ser Cys Lys Asp Ser Gly Gly Thr Phe
                165                 170                 175

Ser Ser Tyr Ala Ile Ser Trp Val Arg Gln Ala Pro Gly Gln Gly Leu
            180                 185                 190

Glu Trp Met Gly Gly Ile Ile Pro Ile Phe Gly Thr Thr Asn Tyr Ala
        195                 200                 205

Gln Gln Phe Gln Gly Arg Val Thr Ile Thr Ala Asp Glu Ser Thr Ser
```

```
            210                 215                 220
Thr Ala Tyr Met Glu Leu Ser Ser Leu Arg Ser Glu Asp Thr Ala Val
225                 230                 235                 240

Tyr Tyr Cys Ala Arg Glu Ala Val Ala Ala Asp Trp Leu Asp Pro Trp
                245                 250                 255

Gly Gln Gly Thr Leu Val Thr Val Ser Ser Phe Val Pro Val Phe Leu
                260                 265                 270

Pro Ala Lys Pro Thr Thr Thr Pro Ala Pro Arg Pro Pro Thr Pro Ala
            275                 280                 285

Pro Thr Ile Ala Ser Gln Pro Leu Ser Leu Arg Pro Glu Ala Cys Arg
        290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Asn His Arg Asn Gln Arg Arg
                340                 345                 350

Lys Tyr Arg Ser Asn Lys Gly Glu Ser Pro Val Glu Pro Ala Glu Pro
            355                 360                 365

Cys Arg Tyr Ser Cys Pro Arg Glu Glu Glu Gly Ser Thr Ile Pro Ile
        370                 375                 380

Gln Glu Asp Tyr Arg Lys Pro Glu Pro Ala Cys Ser Pro Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
                420                 425                 430

Asp Lys Arg Arg Gly Arg Asp Pro Glu Met Gly Gly Lys Pro Arg Arg
            435                 440                 445

Lys Asn Pro Gln Glu Gly Leu Tyr Asn Glu Leu Gln Lys Asp Lys Met
        450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 4
<211> LENGTH: 550
<212> TYPE: PRT
<213> ORGANISM: Artificial Sequence
<220> FEATURE:
<223> OTHER INFORMATION: Synthetic

<400> SEQUENCE: 4

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Thr Leu
                20                  25                  30

Ser Leu Ser Pro Gly Glu Arg Ala Thr Leu Ser Cys Arg Ala Ser Gln
            35                  40                  45

Ser Val Ser Ser Ser Tyr Leu Ala Trp Tyr Gln Gln Lys Pro Gly Gln
        50                  55                  60

Ala Pro Arg Leu Leu Ile Tyr Gly Ala Ser Ser Arg Ala Thr Gly Ile
```

```
                65                  70                  75                  80
        Pro Asp Arg Phe Ser Gly Ser Gly Ser Gly Thr Asp Phe Thr Leu Thr
                            85                  90                  95

Ile Ser Arg Leu Glu Pro Glu Asp Phe Ala Val Tyr Tyr Cys Gln Gln
                            100                 105                 110

Tyr Gly Ser Ser Arg Phe Thr Phe Gly Pro Gly Thr Lys Val Asp Ile
                            115                 120                 125

Lys Gly Ser Thr Ser Gly Ser Gly Lys Pro Gly Ser Gly Glu Gly Ser
                130                 135                 140

Thr Lys Gly Gln Val Gln Leu Val Gln Ser Gly Ala Glu Val Lys Lys
        145                 150                 155                 160

Pro Gly Ser Ser Val Lys Val Ser Cys Lys Asp Ser Gly Gly Thr Phe
                            165                 170                 175

Ser Ser Tyr Ala Ile Ser Trp Val Arg Gln Ala Pro Gly Gln Gly Leu
                            180                 185                 190

Glu Trp Met Gly Gly Ile Ile Pro Ile Phe Gly Thr Thr Asn Tyr Ala
                            195                 200                 205

Gln Gln Phe Gln Gly Arg Val Thr Ile Thr Ala Asp Glu Ser Thr Ser
                            210                 215                 220

Thr Ala Tyr Met Glu Leu Ser Ser Leu Arg Ser Glu Asp Thr Ala Val
        225                 230                 235                 240

Tyr Tyr Cys Ala Arg Glu Ala Val Ala Ala Asp Trp Leu Asp Pro Trp
                            245                 250                 255

Gly Gln Gly Thr Leu Val Thr Val Ser Ser Phe Val Pro Val Phe Leu
                            260                 265                 270

Pro Ala Lys Pro Thr Thr Thr Pro Ala Pro Arg Pro Pro Thr Pro Ala
                            275                 280                 285

Pro Thr Ile Ala Ser Gln Pro Leu Ser Leu Arg Pro Glu Ala Cys Arg
                            290                 295                 300

Pro Ala Ala Gly Gly Ala Val His Thr Arg Gly Leu Asp Phe Ala Cys
        305                 310                 315                 320

Asp Ile Tyr Ile Trp Ala Pro Leu Ala Gly Thr Cys Gly Val Leu Leu
                            325                 330                 335

Leu Ser Leu Val Ile Thr Leu Tyr Cys Asn His Arg Asn Arg Ser Lys
                            340                 345                 350

Arg Ser Arg Leu Leu His Ser Asp Tyr Met Asn Met Thr Pro Arg Arg
                            355                 360                 365

Pro Gly Pro Thr Arg Lys His Tyr Gln Pro Tyr Ala Pro Pro Arg Asp
                370                 375                 380

Phe Ala Ala Tyr Arg Ser Gln Arg Arg Lys Tyr Arg Ser Asn Lys Gly
        385                 390                 395                 400

Glu Ser Pro Val Glu Pro Ala Glu Pro Cys Arg Tyr Ser Cys Pro Arg
                            405                 410                 415

Glu Glu Glu Gly Ser Thr Ile Pro Ile Gln Glu Asp Tyr Arg Lys Pro
                            420                 425                 430

Glu Pro Ala Cys Ser Pro Arg Val Lys Phe Ser Arg Ser Ala Asp Ala
                            435                 440                 445

Pro Ala Tyr Gln Gln Gly Gln Asn Gln Leu Tyr Asn Glu Leu Asn Leu
                            450                 455                 460

Gly Arg Arg Glu Glu Tyr Asp Val Leu Asp Lys Arg Arg Gly Arg Asp
        465                 470                 475                 480

Pro Glu Met Gly Gly Lys Pro Arg Arg Lys Asn Pro Gln Glu Gly Leu
                            485                 490                 495
```

```
Tyr Asn Glu Leu Gln Lys Asp Lys Met Ala Glu Ala Tyr Ser Glu Ile
                500                 505                 510

Gly Met Lys Gly Glu Arg Arg Gly Lys Gly His Asp Gly Leu Tyr
            515                 520                 525

Gln Gly Leu Ser Thr Ala Thr Lys Asp Thr Tyr Asp Ala Leu His Met
530                 535                 540

Gln Ala Leu Pro Pro Arg
545                 550

<210> SEQ ID NO 5
<211> LENGTH: 556
<212> TYPE: PRT
<213> ORGANISM: Artificial Sequence
<220> FEATURE:
<223> OTHER INFORMATION: Synthetic

<400> SEQUENCE: 5

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Thr Leu
                20                  25                  30

Ser Leu Ser Pro Gly Glu Arg Ala Thr Leu Ser Cys Arg Ala Ser Gln
        35                  40                  45

Ser Val Ser Ser Ser Tyr Leu Ala Trp Tyr Gln Gln Lys Pro Gly Gln
    50                  55                  60

Ala Pro Arg Leu Leu Ile Tyr Gly Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
            100                 105                 110

Tyr Gly Ser Ser Arg Phe Thr Phe Gly Pro Gly Thr Lys Val Asp Ile
        115                 120                 125

Lys Gly Ser Thr Ser Gly Ser Gly Lys Pro Gly Ser Gly Glu Gly Ser
    130                 135                 140

Thr Lys Gly Gln Val Gln Leu Val Gln Ser Gly Ala Glu Val Lys Lys
145                 150                 155                 160

Pro Gly Ser Ser Val Lys Val Ser Cys Lys Asp Ser Gly Gly Thr Phe
                165                 170                 175

Ser Ser Tyr Ala Ile Ser Trp Val Arg Gln Ala Pro Gly Gln Gly Leu
            180                 185                 190

Glu Trp Met Gly Gly Ile Ile Pro Ile Phe Gly Thr Thr Asn Tyr Ala
        195                 200                 205

Gln Gln Phe Gln Gly Arg Val Thr Ile Thr Ala Asp Glu Ser Thr Ser
    210                 215                 220

Thr Ala Tyr Met Glu Leu Ser Ser Leu Arg Ser Glu Asp Thr Ala Val
225                 230                 235                 240

Tyr Tyr Cys Ala Arg Glu Ala Val Ala Ala Asp Trp Leu Asp Pro Trp
                245                 250                 255

Gly Gln Gly Thr Leu Val Thr Val Ser Ser Phe Val Pro Val Phe Leu
            260                 265                 270

Pro Ala Lys Pro Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300
```

Pro Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
            325                 330                 335

Leu Ser Leu Val Ile Thr Leu Tyr Cys Asn His Arg Asn Gln Arg Arg
        340                 345                 350

Lys Tyr Arg Ser Asn Lys Gly Glu Ser Pro Val Glu Pro Ala Glu Pro
            355                 360                 365

Cys Arg Tyr Ser Cys Pro Arg Glu Glu Glu Gly Ser Thr Ile Pro Ile
    370                 375                 380

Gln Glu Asp Tyr Arg Lys Pro Glu Pro Ala Cys Ser Pro Arg Phe Ser
385                 390                 395                 400

Val Val Lys Arg Gly Arg Lys Lys Leu Leu Tyr Ile Phe Lys Gln Pro
                405                 410                 415

Phe Met Arg Pro Val Gln Thr Thr Gln Glu Glu Asp Gly Cys Ser Cys
            420                 425                 430

Arg Phe Pro Glu Glu Glu Glu Gly Gly Cys Glu Leu Arg Val Lys Phe
    435                 440                 445

Ser Arg Ser Ala Asp Ala Pro Ala Tyr Gln Gln Gly Gln Asn Gln Leu
    450                 455                 460

Tyr Asn Glu Leu Asn Leu Gly Arg Arg Glu Glu Tyr Asp Val Leu Asp
465                 470                 475                 480

Lys Arg Arg Gly Arg Asp Pro Glu Met Gly Gly Lys Pro Arg Arg Lys
                485                 490                 495

Asn Pro Gln Glu Gly Leu Tyr Asn Glu Leu Gln Lys Asp Lys Met Ala
            500                 505                 510

Glu Ala Tyr Ser Glu Ile Gly Met Lys Gly Glu Arg Arg Arg Gly Lys
            515                 520                 525

Gly His Asp Gly Leu Tyr Gln Gly Leu Ser Thr Ala Thr Lys Asp Thr
            530                 535                 540

Tyr Asp Ala Leu His Met Gln Ala Leu Pro Pro Arg
545                 550                 555

<210> SEQ ID NO 6
<211> LENGTH: 506
<212> TYPE: PRT
<213> ORGANISM: Artificial Sequence
<220> FEATURE:
<223> OTHER INFORMATION: Synthetic

<400> SEQUENCE: 6

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

```
Gly Asn Thr Leu Pro Tyr Thr Phe Gly Gly Gly Thr Lys Leu Glu Ile
            115                 120                 125

Thr Gly Ser Thr Ser Gly Ser Gly Lys Pro Gly Ser Gly Glu Gly Ser
            130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
            195                 200                 205

Ala Leu Lys Ser Arg Leu Thr Ile Ile Lys Asp Asn Ser Lys Ser Gln
            210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Ala Phe Val
            260                 265                 270

Pro Val Phe Leu Pro Ala Lys Pro Thr Thr Thr Pro Ala Pro Arg Pro
            275                 280                 285

Pro Thr Pro Ala Pro Thr Ile Ala Ser Gln Pro Leu Ser Leu Arg Pro
            290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Ser Lys Arg Ser Arg Leu Leu His Ser Asp Tyr Met Asn Met
            355                 360                 365

Thr Pro Arg Arg Pro Gly Pro Thr Arg Lys His Tyr Gln Pro Tyr Ala
            370                 375                 380

Pro Pro Arg Asp Phe Ala Ala Tyr Arg Ser Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
            435                 440                 445

Gln Glu Gly Leu Tyr Asn Glu Leu Gln Lys Asp Lys Met Ala Glu Ala
            450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
            500                 505

<210> SEQ ID NO 7
<211> LENGTH: 560
```

```
<212> TYPE: PRT
<213> ORGANISM: Artificial Sequence
<220> FEATURE:
<223> OTHER INFORMATION: Synthetic

<400> SEQUENCE: 7

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Gln Arg Arg Lys Tyr Arg Ser Asn Lys Gly Glu Ser Pro Val Glu
        355                 360                 365

Pro Ala Glu Pro Cys Arg Tyr Ser Cys Pro Arg Glu Glu Glu Gly Ser
    370                 375                 380
```

```
Thr Ile Pro Ile Gln Glu Asp Tyr Arg Lys Pro Glu Pro Ala Cys Ser
385                 390                 395                 400

Pro Arg Phe Ser Val Val Lys Arg Gly Arg Lys Lys Leu Leu Tyr Ile
                405                 410                 415

Phe Lys Gln Pro Phe Met Arg Pro Val Gln Thr Thr Gln Glu Glu Asp
            420                 425                 430

Gly Cys Ser Cys Arg Phe Pro Glu Glu Glu Glu Gly Gly Cys Glu Leu
            435                 440                 445

Arg Val Lys Phe Ser Arg Ser Ala Asp Ala Pro Ala Tyr Gln Gln Gly
        450                 455                 460

Gln Asn Gln Leu Tyr Asn Glu Leu Asn Leu Gly Arg Arg Glu Glu Tyr
465                 470                 475                 480

Asp Val Leu Asp Lys Arg Arg Gly Arg Asp Pro Glu Met Gly Gly Lys
                485                 490                 495

Pro Arg Arg Lys Asn Pro Gln Glu Gly Leu Tyr Asn Glu Leu Gln Lys
            500                 505                 510

Asp Lys Met Ala Glu Ala Tyr Ser Glu Ile Gly Met Lys Gly Glu Arg
            515                 520                 525

Arg Arg Gly Lys Gly His Asp Gly Leu Tyr Gln Gly Leu Ser Thr Ala
        530                 535                 540

Thr Lys Asp Thr Tyr Asp Ala Leu His Met Gln Ala Leu Pro Pro Arg
545                 550                 555                 560

<210> SEQ ID NO 8
<211> LENGTH: 513
<212> TYPE: PRT
<213> ORGANISM: Artificial Sequence
<220> FEATURE:
<223> OTHER INFORMATION: Synthetic

<400> SEQUENCE: 8

Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190
```

```
Glu Trp Leu Gly Val Ile Trp Gly Ser Glu Thr Thr Tyr Tyr Asn Ser
            195                 200                 205

Ala Leu Lys Ser Arg Leu Thr Ile Ile Lys Asp Asn Ser Lys Ser Gln
        210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Phe Val
                260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
        290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Gln Arg Arg Lys Tyr Arg Ser Asn Lys Gly Glu Ser Pro Val Glu
        355                 360                 365

Pro Ala Glu Pro Cys Arg Tyr Ser Cys Pro Arg Glu Glu Glu Gly Ser
        370                 375                 380

Thr Ile Pro Ile Gln Glu Asp Tyr Arg Lys Pro Glu Pro Ala Cys Ser
385                 390                 395                 400

Pro Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
                420                 425                 430

Tyr Asp Val Leu Asp Lys Arg Arg Gly Arg Asp Pro Glu Met Gly Gly
                435                 440                 445

Lys Pro Arg Arg Lys Asn Pro Gln Glu Gly Leu Tyr Asn Glu Leu Gln
450                 455                 460

Lys Asp Lys Met Ala Glu Ala Tyr Ser Glu Ile Gly Met Lys Gly Glu
465                 470                 475                 480

Arg Arg Arg Gly Lys Gly His Asp Gly Leu Tyr Gln Gly Leu Ser Thr
                485                 490                 495

Ala Thr Lys Asp Thr Tyr Asp Ala Leu His Met Gln Ala Leu Pro Pro
                500                 505                 510

Arg

<210> SEQ ID NO 9
<211> LENGTH: 554
<212> TYPE: PRT
<213> ORGANISM: Artificial Sequence
<220> FEATURE:
<223> OTHER INFORMATION: Synthetic

<400> SEQUENCE: 9

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
```

```
                35                  40                  45
Gln Asp Ile Ser Lys Tyr Leu Asn Trp Tyr Gln Gln Lys Pro Asp Gly
 50                  55                  60

Thr Val Lys Leu Leu Ile Tyr His Thr Ser Arg Leu His Ser Gly Val
 65                  70                  75                  80

Pro Ser Arg Phe Ser Gly Ser Gly Ser Gly Thr Asp Tyr Ser Leu Thr
                 85                  90                  95

Ile Ser Asn Leu Glu Gln Glu Asp Ile Ala Thr Tyr Phe Cys Gln Gln
                100                 105                 110

Gly Asn Thr Leu Pro Tyr Thr Phe Gly Gly Gly Thr Lys Leu Glu Ile
                115                 120                 125

Thr Gly Ser Thr Ser Gly Ser Gly Lys Pro Gly Ser Gly Glu Gly Ser
 130                 135                 140

Thr Lys Gly Glu Val Lys Leu Gln Glu Ser Gly Pro Gly Leu Val Ala
 145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
                180                 185                 190

Glu Trp Leu Gly Val Ile Trp Gly Ser Glu Thr Thr Tyr Tyr Asn Ser
                195                 200                 205

Ala Leu Lys Ser Arg Leu Thr Ile Ile Lys Asp Asn Ser Lys Ser Gln
 210                 215                 220

Val Phe Leu Lys Met Asn Ser Leu Gln Thr Asp Asp Thr Ala Ile Tyr
 225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Ala Phe Val
                260                 265                 270

Pro Val Phe Leu Pro Ala Lys Pro Thr Thr Thr Pro Ala Pro Arg Pro
                275                 280                 285

Pro Thr Pro Ala Pro Thr Ile Ala Ser Gln Pro Leu Ser Leu Arg Pro
 290                 295                 300

Glu Ala Cys Arg Pro Ala Ala Gly Gly Ala Val His Thr Arg Gly Leu
 305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
                340                 345                 350

Asn Arg Ser Lys Arg Ser Arg Leu Leu His Ser Asp Tyr Met Asn Met
                355                 360                 365

Thr Pro Arg Arg Pro Gly Pro Thr Arg Lys His Tyr Gln Pro Tyr Ala
                370                 375                 380

Pro Pro Arg Asp Phe Ala Ala Tyr Arg Ser Gln Arg Arg Lys Tyr Arg
 385                 390                 395                 400

Ser Asn Lys Gly Glu Ser Pro Val Glu Pro Ala Glu Pro Cys Arg Tyr
                405                 410                 415

Ser Cys Pro Arg Glu Glu Glu Gly Ser Thr Ile Pro Ile Gln Glu Asp
                420                 425                 430

Tyr Arg Lys Pro Glu Pro Ala Cys Ser Pro Arg Val Lys Phe Ser Arg
                435                 440                 445

Ser Ala Asp Ala Pro Ala Tyr Gln Gln Gly Gln Asn Gln Leu Tyr Asn
 450                 455                 460
```

```
Glu Leu Asn Leu Gly Arg Arg Glu Glu Tyr Asp Val Leu Asp Lys Arg
465                 470                 475                 480

Arg Gly Arg Asp Pro Glu Met Gly Gly Lys Pro Arg Lys Asn Pro
                485                 490                 495

Gln Glu Gly Leu Tyr Asn Glu Leu Gln Lys Asp Lys Met Ala Glu Ala
                500                 505                 510

Tyr Ser Glu Ile Gly Met Lys Gly Glu Arg Arg Arg Gly Lys Gly His
            515                 520                 525

Asp Gly Leu Tyr Gln Gly Leu Ser Thr Ala Thr Lys Asp Thr Tyr Asp
530                 535                 540

Ala Leu His Met Gln Ala Leu Pro Pro Arg
545                 550

<210> SEQ ID NO 10
<211> LENGTH: 476
<212> TYPE: PRT
<213> ORGANISM: Artificial Sequence
<220> FEATURE:
<223> OTHER INFORMATION: Synthetic

<400> SEQUENCE: 10

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Thr Leu
                20                  25                  30

Ser Leu Ser Pro Gly Glu Arg Ala Thr Leu Ser Cys Arg Ala Ser Gln
            35                  40                  45

Ser Val Ser Ser Ser Tyr Leu Ala Trp Tyr Gln Gln Lys Pro Gly Gln
        50                  55                  60

Ala Pro Arg Leu Leu Ile Tyr Gly Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
                100                 105                 110

Tyr Gly Ser Ser Arg Phe Thr Phe Gly Pro Gly Thr Lys Val Asp Ile
            115                 120                 125

Lys Gly Ser Thr Ser Gly Ser Gly Lys Pro Gly Ser Gly Glu Gly Ser
        130                 135                 140

Thr Lys Gly Gln Val Gln Leu Val Gln Ser Gly Ala Glu Val Lys Lys
145                 150                 155                 160

Pro Gly Ser Ser Val Lys Val Ser Cys Lys Asp Ser Gly Gly Thr Phe
                165                 170                 175

Ser Ser Tyr Ala Ile Ser Trp Val Arg Gln Ala Pro Gly Gln Gly Leu
            180                 185                 190

Glu Trp Met Gly Gly Ile Ile Pro Ile Phe Gly Thr Thr Asn Tyr Ala
        195                 200                 205

Gln Gln Phe Gln Gly Arg Val Thr Ile Thr Ala Asp Glu Ser Thr Ser
    210                 215                 220

Thr Ala Tyr Met Glu Leu Ser Ser Leu Arg Ser Glu Asp Thr Ala Val
225                 230                 235                 240

Tyr Tyr Cys Ala Arg Glu Ala Val Ala Ala Asp Trp Leu Asp Pro Trp
                245                 250                 255

Gly Gln Gly Thr Leu Val Thr Val Ser Ser Phe Val Pro Val Phe Leu
            260                 265                 270
```

-continued

Pro Ala Lys Pro Thr Thr Thr Pro Ala Pro Arg Pro Pro Thr Pro Ala
            275                 280                 285

Pro Thr Ile Ala Ser Gln Pro Leu Ser Leu Arg Pro Glu Ala Cys Arg
            290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
            325                 330                 335

Leu Ser Leu Val Ile Thr Leu Tyr Cys Asn His Arg Asn Arg Ser Lys
            340                 345                 350

Arg Ser Arg Leu Leu His Ser Asp Tyr Met Asn Met Thr Pro Arg Arg
            355                 360                 365

Pro Gly Pro Thr Arg Lys His Tyr Gln Pro Tyr Ala Pro Pro Arg Asp
            370                 375                 380

Phe Ala Ala Tyr Arg Ser Gln Arg Arg Lys Tyr Arg Ser Asn Lys Gly
385                 390                 395                 400

Glu Ser Pro Val Glu Pro Ala Glu Pro Cys Arg Tyr Ser Cys Pro Arg
            405                 410                 415

Glu Glu Glu Gly Ser Thr Ile Pro Ile Gln Glu Asp Tyr Arg Lys Pro
            420                 425                 430

Glu Pro Ala Cys Ser Pro Gln Val Arg Lys Ala Ala Ile Thr Ser Tyr
            435                 440                 445

Glu Lys Ser Asp Gly Val Tyr Thr Gly Leu Ser Thr Arg Asn Gln Glu
450                 455                 460

Thr Tyr Glu Thr Leu Lys His Glu Lys Pro Pro Gln
465                 470                 475

<210> SEQ ID NO 11
<211> LENGTH: 480
<212> TYPE: PRT
<213> ORGANISM: Artificial Sequence
<220> FEATURE:
<223> OTHER INFORMATION: Synthetic

<400> SEQUENCE: 11

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
        50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
            85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
            115                 120                 125

Thr Gly Ser Thr Ser Gly Ser Gly Lys Pro Gly Ser Gly Glu Gly Ser
        130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Ala Phe Val
                260                 265                 270

Pro Val Phe Leu Pro Ala Lys Pro Thr Thr Thr Pro Ala Pro Arg Pro
            275                 280                 285

Pro Thr Pro Ala Pro Thr Ile Ala Ser Gln Pro Leu Ser Leu Arg Pro
        290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Gln Arg Arg Lys Tyr Arg
385                 390                 395                 400

Ser Asn Lys Gly Glu Ser Pro Val Glu Pro Ala Glu Pro Cys Arg Tyr
                405                 410                 415

Ser Cys Pro Arg Glu Glu Glu Gly Ser Thr Ile Pro Ile Gln Glu Asp
            420                 425                 430

Tyr Arg Lys Pro Glu Pro Ala Cys Ser Pro Gln Val Arg Lys Ala Ala
        435                 440                 445

Ile Thr Ser Tyr Glu Lys Ser Asp Gly Val Tyr Thr Gly Leu Ser Thr
    450                 455                 460

Arg Asn Gln Glu Thr Tyr Glu Thr Leu Lys His Glu Lys Pro Pro Gln
465                 470                 475                 480

<210> SEQ ID NO 12
<211> LENGTH: 428
<212> TYPE: PRT
<213> ORGANISM: Artificial Sequence
<220> FEATURE:
<223> OTHER INFORMATION: Synthetic

<400> SEQUENCE: 12

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Thr Leu
            20                  25                  30

Ser Leu Ser Pro Gly Glu Arg Ala Thr Leu Ser Cys Arg Ala Ser Gln
        35                  40                  45

Ser Val Ser Ser Ser Tyr Leu Ala Trp Tyr Gln Gln Lys Pro Gly Gln
 50                  55                  60

Ala Pro Arg Leu Leu Ile Tyr Gly Ala Ser Ser Arg Ala Thr Gly Ile
 65                  70                  75                  80

Pro Asp Arg Phe Ser Gly Ser Gly Ser Gly Thr Asp Phe Thr Leu Thr
                 85                  90                  95

Ile Ser Arg Leu Glu Pro Glu Asp Phe Ala Val Tyr Tyr Cys Gln Gln
            100                 105                 110

Tyr Gly Ser Ser Arg Phe Thr Phe Gly Pro Gly Thr Lys Val Asp Ile
        115                 120                 125

Lys Gly Ser Thr Ser Gly Ser Gly Lys Pro Gly Ser Gly Glu Gly Ser
    130                 135                 140

Thr Lys Gly Gln Val Gln Leu Val Gln Ser Gly Ala Glu Val Lys Lys
145                 150                 155                 160

Pro Gly Ser Ser Val Lys Val Ser Cys Lys Asp Ser Gly Gly Thr Phe
                165                 170                 175

Ser Ser Tyr Ala Ile Ser Trp Val Arg Gln Ala Pro Gly Gln Gly Leu
            180                 185                 190

Glu Trp Met Gly Gly Ile Ile Pro Ile Phe Gly Thr Thr Asn Tyr Ala
        195                 200                 205

Gln Gln Phe Gln Gly Arg Val Thr Ile Thr Ala Asp Glu Ser Thr Ser
    210                 215                 220

Thr Ala Tyr Met Glu Leu Ser Ser Leu Arg Ser Glu Asp Thr Ala Val
225                 230                 235                 240

Tyr Tyr Cys Ala Arg Glu Ala Val Ala Ala Asp Trp Leu Asp Pro Trp
                245                 250                 255

Gly Gln Gly Thr Leu Val Thr Val Ser Ser Phe Val Pro Val Phe Leu
            260                 265                 270

Pro Ala Lys Pro Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Asn His Arg Asn Arg Ser Lys
            340                 345                 350

Arg Ser Arg Leu Leu His Ser Asp Tyr Met Asn Met Thr Pro Arg Arg
        355                 360                 365

Pro Gly Pro Thr Arg Lys His Tyr Gln Pro Tyr Ala Pro Pro Arg Asp
    370                 375                 380

Phe Ala Ala Tyr Arg Ser Gln Val Arg Lys Ala Ala Ile Thr Ser Tyr
385                 390                 395                 400

Glu Lys Ser Asp Gly Val Tyr Thr Gly Leu Ser Thr Arg Asn Gln Glu
                405                 410                 415

Thr Tyr Glu Thr Leu Lys His Glu Lys Pro Pro Gln
            420                 425

<210> SEQ ID NO 13
<211> LENGTH: 432
<212> TYPE: PRT
<213> ORGANISM: Artificial Sequence
<220> FEATURE:

<223> OTHER INFORMATION: Synthetic

<400> SEQUENCE: 13

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Gln Val Arg Lys Ala Ala
385                 390                 395                 400
```

-continued

```
Ile Thr Ser Tyr Glu Lys Ser Asp Gly Val Tyr Thr Gly Leu Ser Thr
                405                 410                 415

Arg Asn Gln Glu Thr Tyr Glu Thr Leu Lys His Glu Lys Pro Pro Gln
            420                 425                 430

<210> SEQ ID NO 14
<211> LENGTH: 18
<212> TYPE: PRT
<213> ORGANISM: Artificial Sequence
<220> FEATURE:
<223> OTHER INFORMATION: Synthetic

<400> SEQUENCE: 14

Gly Ser Thr Ser Gly Ser Gly Lys Pro Gly Ser Gly Glu Gly Ser Thr
1               5                   10                  15

Lys Gly

<210> SEQ ID NO 15
<211> LENGTH: 47
<212> TYPE: PRT
<213> ORGANISM: Artificial Sequence
<220> FEATURE:
<223> OTHER INFORMATION: Synthetic

<400> SEQUENCE: 15

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Gly Gly Cys Glu Leu
        35                  40                  45
```

CHIMERIC ANTIGEN RECEPTORS TARGETING CD-19

CROSS-REFERENCE TO RELATED APPLICATIONS

This patent application is a Continuation Application of U.S. patent application Ser. No. 15/315,533, filed Dec. 1, 2016, which is a U.S. National Phase of International Patent Application No. PCT/US2015/033473, filed Jun. 1, 2015, which claims the benefit of U.S. Provisional Patent Application No. 62/006,313, filed Jun. 2, 2014, each of which is incorporated herein by reference in its entirety.

STATEMENT REGARDING FEDERALLY SPONSORED RESEARCH AND DEVELOPMENT

This invention was made with Government support under project number Z01 BC001415 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 58,446 Byte ASCII (Text) file named "742192_ST25.txt," created on Mar. 15, 2019.

BACKGROUND OF THE INVENTION

B-cell malignancies, such as lymphoma and leukemia, occur when the regulation of B-cell differentiation and activation is disrupted. Malignancies of mature B-cells include follicular lymphoma, mantle-cell lymphoma, Burkitt lymphoma, multiple myeloma, diffuse large B-cell lymphoma, Hodgkin lymphoma, lymphoplasmacytic lymphoma, marginal-zone lymphoma, and chronic lymphocytic leukemia (Shaffer et al., *Nature Reviews Immunology*, 2: 920-933 (2002)). Standard therapies such as chemotherapy, therapeutic monoclonal antibodies (e.g., Rituximab (RITUXAN™)), and allogeneic stem cell transplantation (alloH-SCT) do not cure B-cell malignancies (see, e.g., Dreger et al., *Leukemia*, 21(1): 12-17 (2007); Gribben, J. G., *Blood*, 109(11): 4617-4626 (2007); and Armitage, J. O., *Blood*, 110(1): 29-36 (2007)). In particular, monoclonal antibodies are not curative as single agents, and alloHSCT is associated with high levels of mortality and morbidity (see, e.g., Dreger et al., supra, Armitage et al., supra, and McLaughlin et al., *Journal of Clinical Oncology*, 16(8): 2825-2833 (1998)).

T-cells can be genetically modified to express chimeric antigen receptors (CARs), which are fusion proteins comprised of an antigen recognition moiety and T-cell activation domains (see, e.g., Kershaw et al., supra, Eshhar et al., *Proc. Natl. Acad. Sci. USA*, 90(2): 720-724 (1993), and Sadelain et al., *Curr. Opin. Immunol.*, 21(2): 215-223 (2009)). For B-cell lineage malignancies, adoptive T-cell approaches that utilize CARs which target CD19 have been developed (see, e.g., Jensen et al., *Biology of Blood and Marrow Transplantation*, 16: 1245-1256 (2010); Kochenderfer et al., *Blood*, 116(20): 4099-4102 (2010); Porter et al., *The New England Journal of Medicine*, 365(8): 725-733 (2011); Savoldo et al., *Journal of Clinical Investigation*, 121(5): 1822-1826 (2011), Cooper et al., *Blood*, 101(4): 1637-1644 (2003); Brentjens et al., *Nature Medicine*, 9(3): 279-286 (2003); Kalos et al., *Science Translational Medicine*, 3(95): 95ra73 (2011); Cheadle et al., *Journal of Immunology*, 184(4): 1885-1896 (2010); Brentjens et al., *Clinical Cancer Research*, 13 (18 Pt 1): 5426-5435 (2007); Kochenderfer et al., *Blood*, 116(19): 3875-3886 (2010); Brentjens et al., *Blood*, 118(18): 4817-4828 (2011); and Kochenderfer et al., *Blood*, Dec. 8, 2011 (epublication ahead of print (2012)). The B-cell antigen CD19 has been chosen as target for CARs because its expression is limited to normal and malignant B-cells (see, e.g., Nadler et al., *Journal of Immunology*, 131(1): 244-250 (1983)).

One disadvantage associated with the anti-CD19 CAR therapies reported to date is that they can induce significant toxicity associated with elevated levels of serum cytokines. The generation of human anti-mouse immune responses also is a potential risk associated with current anti-CD19 CARs, which contain murine sequences (see, e.g., Jensen et al., supra; Lamers et al., *Blood*, 117(1): 72-82 (2011); and Maus et al., *Cancer Immunol Res*, 2: 112-120 (2014)).

Thus, there remains a need for compositions that can be used in methods to treat B-cell malignancies which have reduced toxicity and immunogenicity in humans. This invention provides such compositions and methods.

BRIEF SUMMARY OF THE INVENTION

The invention provides an isolated or purified chimeric antigen receptor (CAR) directed against CD19, which comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

In addition, the invention provides isolated or purified nucleic acid sequences encoding the foregoing CARs, vectors comprising such nucleic acid sequences, isolated T-cells comprising such vectors, and methods of destroying malignant B-cells by contacting such isolated T-cells with a population of malignant CD19-expressing B-cells cells in vivo or ex vivo.

The invention also provides an isolated or purified CAR comprising the following elements that are present in SEQ ID NO: 4 or SEQ ID NO: 9: (i) the extracellular spacer, (i) the transmembrane domain derived from a human CD8α molecule, and (iii) the intracellular T-cell signaling domains derived from a human CD28 molecule, a human CD27 molecule, and a human CD3ζ molecule.

The invention provides an isolated or purified CAR comprising the following elements that are present in SEQ ID NO: 10 or SEQ ID NO: 11: (i) the extracellular spacer, (i) the transmembrane domain derived from a human CD8α molecule, and (iii) the intracellular T-cell signaling domains derived from a human CD28 molecule, a human CD27 molecule, and the gamma chain of FcεRI.

BRIEF DESCRIPTION OF THE SEVERAL VIEWS OF THE DRAWING(S)

FIG. 1 is a graph depicting experimental results illustrating in vitro survival of T-cells expressing the indicated CARs as described in Example 2. The percentages of T-cells expressing the indicated CARs on day 7 of culture were as follows: FMC63-28Z, 71%; FMC63-CD828Z, 88%; and FMC63-CD8BBZ, 87%.

FIGS. 2A-2D are images of FACs plots which illustrate expression of the indicated fully human CARs comprising CD27 intracellular signaling domains on the surface of T-cells. The plots are gated on live CD3+ lymphocytes.

Figure 3A:
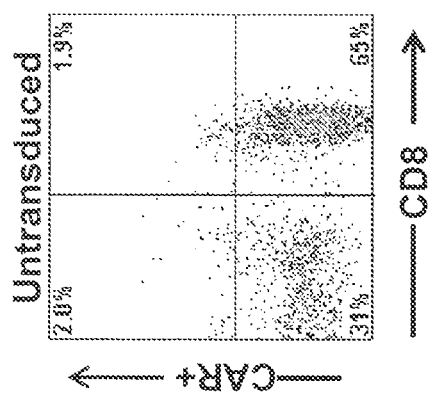
FIGS. 3A and 3B are images of FACs plots which illustrate expression of the 47G4-CD828Z CAR (FIG. 3A) on the surface of T-cells compared to untransduced control (FIG. 3B). The plots are gated on live CD3+ lymphocytes.
Figure 3B:
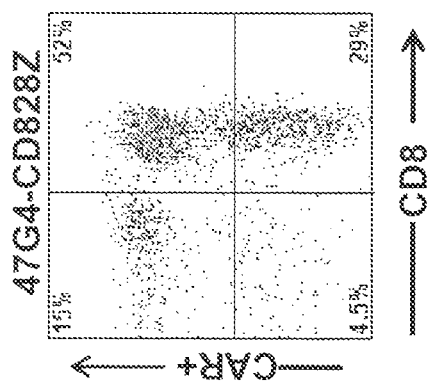
Figure 4A:
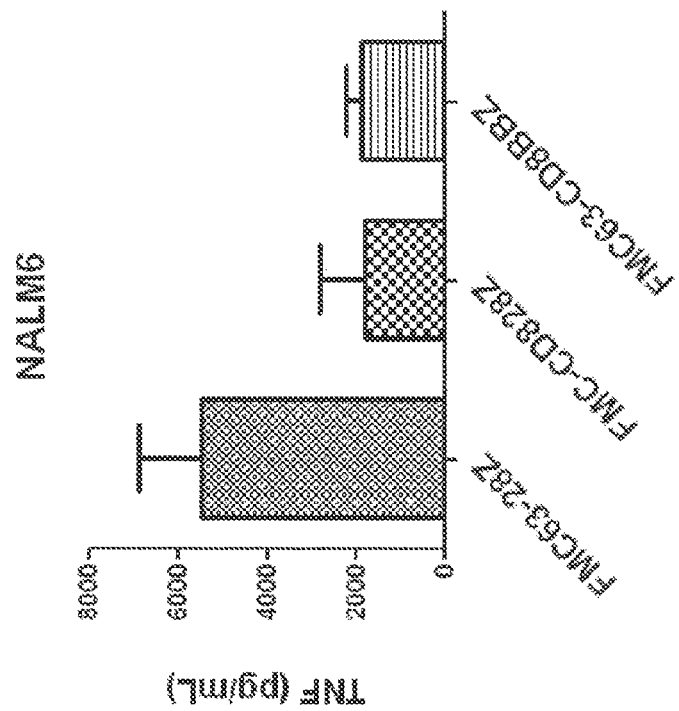
Figure 4B:
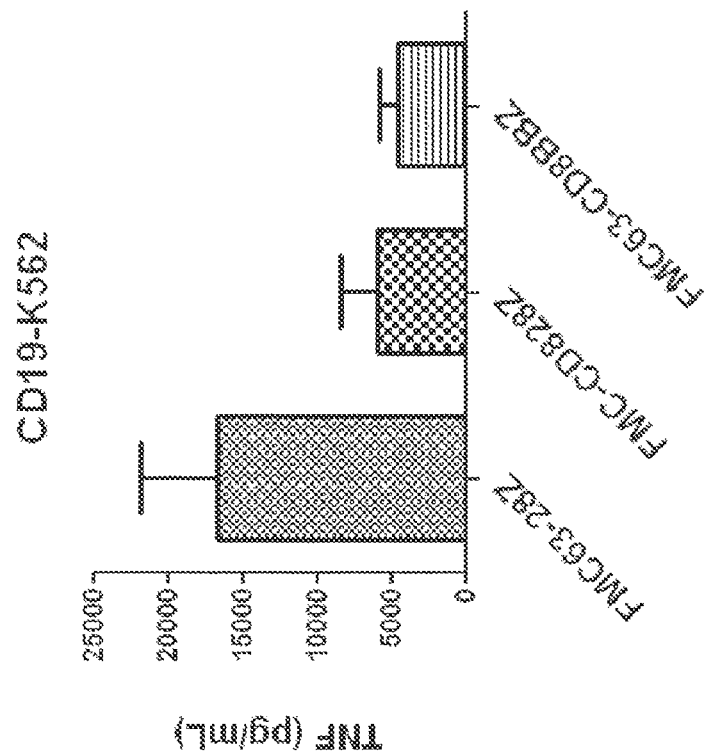
Figure 6A:
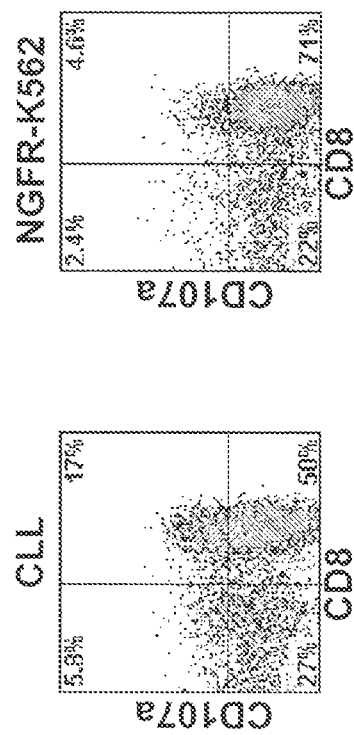
Figure 6B:
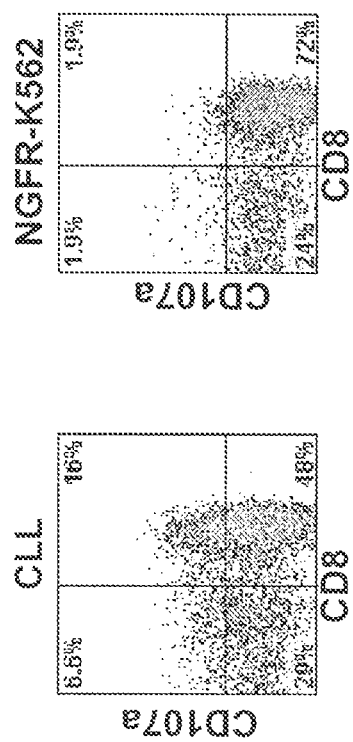
Figure 6C:
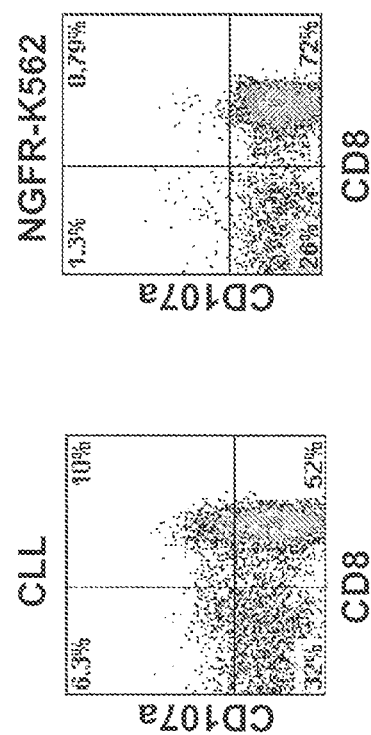
Figure 6D:
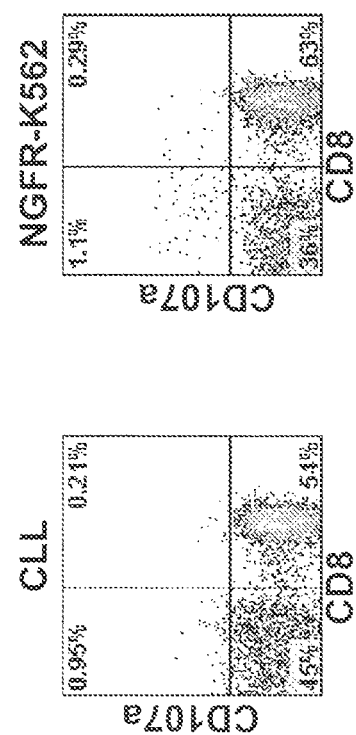

FIGS. 4A and 4B are graphs depicting experimental results illustrating the production of TNF by T-cells expressing the FMC63-28Z, FMC63-CD828Z, or FMC63-CD8BBZ CARs in CD19+ T-cell lines CD19-K562 (FIG. 3A) and NALM6 (FIG. 3B). A standard TNF ELISA was conducted to measure the amount of TNF (pg/mL) in the culture supernatants. The TNF level was normalized to the fraction of T-cells in each culture that expressed each CAR. The results show the mean and standard error of the mean of normalized TNF levels from two different donors.

FIG. 5 is a graph depicting experimental results illustrating the production of IFNγ by T-cells expressing the 47G4-CD828Z CAR in CD19+ T-cell lines CD19-K562 and NALM6. A549, TC71, and CCRF-CEM are CD19-negative cell lines.

FIGS. 6A-6D are FACs plots which illustrate that T-cells transduced with the indicated CARs degranulated in a CD19-specific manner, as measured by CD107a upregulation.

Figure 7A:
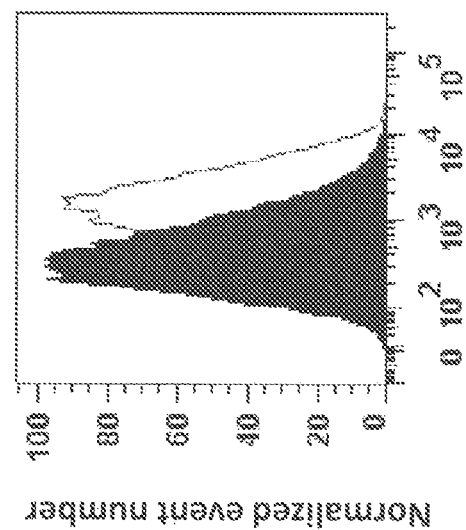
Figure 7B:
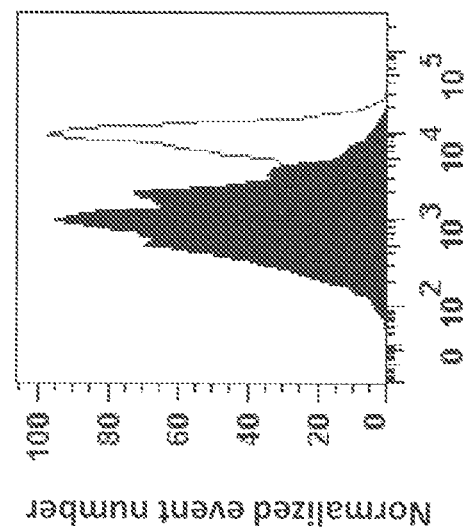
Figure 7C:
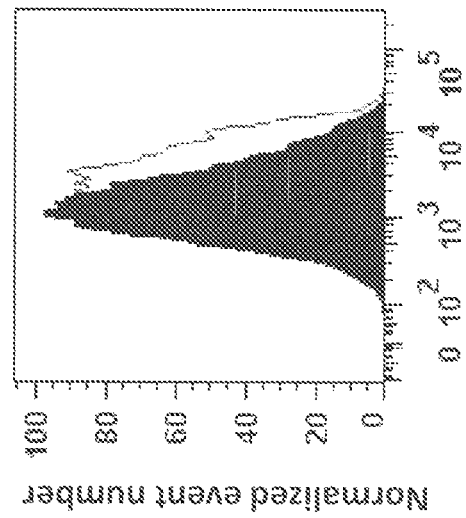

FIGS. 7A-7C are FACs plots which illustrate that T-cells expressing the indicated CARs can proliferate in response to CD19 as measured by carboxyfluorescein diacetate succinimidyl ester (CFSE) fluorescence. T-cells expressing the indicated CARs were cultured with either the CD19+ cell line CD19-K562 (black filled curve) or the CD19-negative cell line NGFR-K562 (open curve) in media that did not contain IL-2 for four days. All plots are gated on live CD3+CAR+ lymphocytes.

Figure 8:
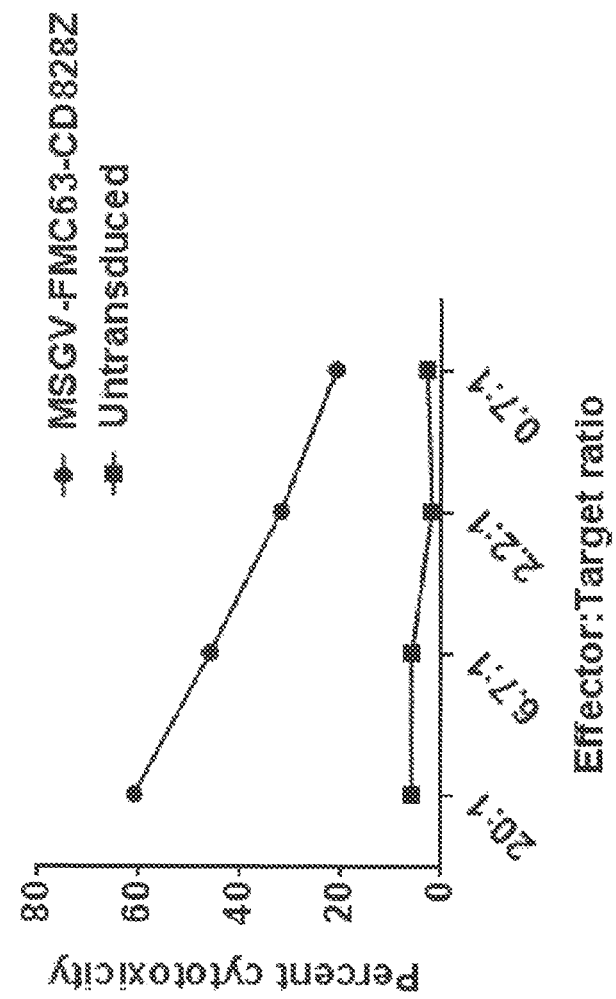

FIG. 8 is a graph which depicts experimental results illustrating that T-cells transduced with the MSGV-FMC63-CD828Z plasmid, which encodes the FMC63-CD828Z CAR, are cytotoxic to primary chronic lymphocytic leukemia (CLL) cells.

Figure 9:
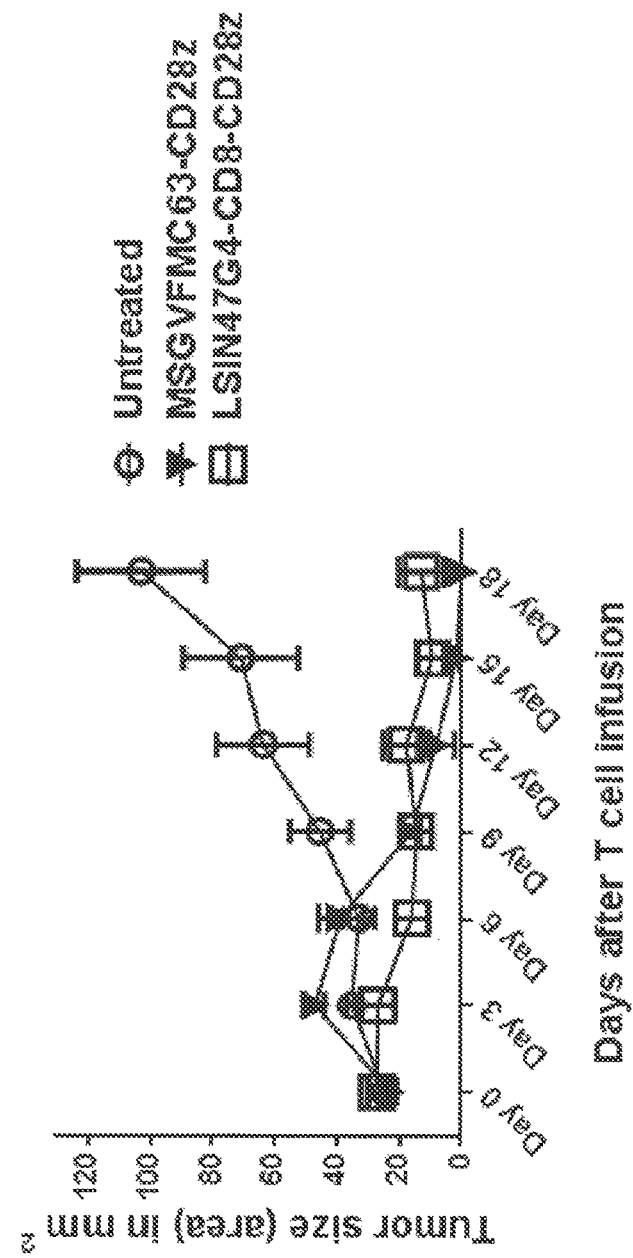

FIG. 9 is a graph which depicts experimental results illustrating that T-cells expressing either the FMC63-28Z CAR or the 47G4-CD8CD28Z CAR reduce the size of NALM6 tumors in NSG immunocompromised mice.

DETAILED DESCRIPTION OF THE INVENTION

The invention provides an isolated or purified chimeric antigen receptor (CAR), wherein the CAR comprises an antigen recognition moiety and a T-cell activation moiety. A chimeric antigen receptor (CAR) is an artificially constructed hybrid protein or polypeptide containing an antigen binding domain of an antibody (e.g., a single chain variable fragment (scFv)) linked to T-cell signaling or T-cell activation domains. CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains.

By "isolated" is meant the removal of a substance (e.g., a protein or nucleic acid) from its natural environment. By "purified" is meant that a given substance (e.g., a protein or nucleic acid), whether one that has been removed from nature (e.g., genomic DNA and mRNA) or synthesized (e.g., cDNA) and/or amplified under laboratory conditions, has been increased in purity, wherein "purity" is a relative term, not "absolute purity." It is to be understood, however, that nucleic acids and proteins may be formulated with diluents or adjuvants and still for practical purposes be isolated. For example, proteins typically are mixed with an acceptable carrier or diluent when used for introduction into cells.

The inventive CAR comprises an antigen recognition moiety that is directed against CD19 (also known as B-lymphocyte antigen CD19, B4, and CVID3). CD19 is a cell surface molecule expressed only by B lymphocytes and follicular dendritic cells of the hematopoietic system. It is the earliest of the B-lineage-restricted antigens to be expressed and is present on most pre-B-cells and most non-T-cell acute lymphocytic leukemia cells and B-cell type chronic lymphocytic leukemia cells (Tedder and Isaacs, *J. Immun.*, 143: 712-717 (1989)). CD19 primarily acts as a B-cell co-receptor in conjunction with CD21 and CD81 (Bradbury et al., *J. Immunol.*, 149(9): 2841-2850 (1992); Horvath et al., *J. Biol. Chem.*, 273 (46): 30537-30543 (1998); and Imai et al., *J. Immunol.*, 155 (3): 1229-1239 (1995)). Upon activation, the cytoplasmic tail of CD19 becomes phosphorylated, which leads to binding by Src-family kinases and recruitment of PI-3 kinase. CD19 also has been shown to interact with other cell signaling proteins, such as the Lyn tyrosine protein kinase, which is the predominant Src kinase in B-cells (Fujimoto et al., *Immunity*, 13: 47-57 (2000)), CD82 (Imai et al., supra), complement receptor 2 (Bradbury et al., supra; and Horvath et al., supra), and VAV2 (Doody et al., *EMBO J.*, 19 (22): 6173-6184 (2000)).

The inventive CAR comprises an antigen recognition moiety that contains a monoclonal antibody directed against CD19, or an antigen-binding portion thereof. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. The antigen recognition moiety of the inventive CAR can be a whole antibody or an antibody fragment. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have the same general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

The terms "fragment of an antibody," "antibody fragment," "functional fragment of an antibody," and "antigen-binding portion" are used interchangeably herein to mean one or more fragments or portions of an antibody that retain the ability to specifically bind to an antigen (see, generally, Holliger et al., *Nat. Biotech.*, 23(9): 1126-1129 (2005)). The antigen recognition moiety of the inventive CAR can contain any CD19-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the hinge region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., *Science,* 242: 423-426 (1988); Huston et al., *Proc. Natl. Acad. Sci. USA,* 85: 5879-5883 (1988); and Osbourn et al., *Nat. Biotechnol.,* 16: 778 (1998)), and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Patent Application Publication 2009/0093024 A1. In a preferred embodiment, the antigen recognition moiety of the inventive CAR comprises an anti-CD19 single chain Fv (scFv).

An antigen-binding portion or fragment of a monoclonal antibody can be of any size so long as the portion binds to CD19. In this respect, an antigen binding portion or fragment of the monoclonal antibody directed against CD19 (also referred to herein as an "anti-CD19 monoclonal antibody") desirably comprises one or more CDRs comprising between about 5 and 18 amino acids (e.g., about 5, 6, 7, 8, 9, 10, 11, 12, 13, 14, 15, 16, 17, 18, or a range defined by any two of the foregoing values).

In one embodiment, the inventive CAR comprises an antigen recognition moiety that comprises a variable region of an anti-CD19 monoclonal antibody. The anti-CD19 monoclonal antibody can be obtained or derived from a mammal, including but not limited to, a mouse, a rat, or a human. Preferably, the antigen recognition moiety comprises a variable region of a mouse or human anti-CD19 monoclonal antibody. In this respect, the antigen recognition moiety comprises a light chain variable region, a heavy chain variable region, or both a light chain variable region and a heavy chain variable region of a mouse or human anti-CD19 monoclonal antibody. Preferably, the antigen recognition moiety of the inventive CAR comprises a light chain variable region and a heavy chain variable region of a mouse or human anti-CD19 monoclonal antibody. The FMC63 antibody (described in Nicholson et al., *Molecular Immunology,* 34(16-17): 1157-1165 (1997)) is one example of a murine anti-CD19 monoclonal antibody that can be used in the present invention. Variable regions of the FMC63 monoclonal antibody have been utilized in CARs that have been tested in clinical trials (see, e.g., Kochenderfer et al., *Nature Review Clinical Oncol.,* 10(5); 267-276 (2013); Porter et al., *New Eng. J. Med.,* 365(8): 725-733 (2011); Kalos et al., *Science Translational Medicine,* 3(95): 95ra73 (2011); Kochenderfer et al., *Blood,* 116(20): 4099-4102 (2010); and Kochenderfer et al., *Blood,* 119(12): 2709-2720 (2012)). The 47G4 antibody (described in U.S Patent Application Publication No. 2010/0104509) is one example of a human anti-CD19 monoclonal antibody that can be used in the present invention.

In another embodiment, the inventive CAR comprises a signal sequence. The signal sequence may be positioned at the amino terminus of the antigen recognition moiety (e.g., the variable region of the anti-CD19 antibody). The signal sequence may comprise any suitable signal sequence. In one embodiment, the signal sequence is a human granulocyte-macrophage colony-stimulating factor (GM-CSF) receptor signal sequence or a CD8α signal sequence. For example, an inventive CAR comprising a murine anti-CD19 scFv can comprise a GM-CSF signal sequence, while an inventive CAR comprising a human anti-CD19 scFv can comprise a CD8α signal sequence.

In another embodiment, the inventive CAR comprises an extracellular spacer sequence. The extracellular spacer sequence is a short sequence of amino acids that facilitates antibody flexibility (see, e.g., Woof et al., *Nat. Rev. Immunol.,* 4(2): 89-99 (2004)), and may be positioned between the antigen recognition moiety (e.g., an anti-CD19 scFv) and the T-cell activation moiety. The extracellular spacer sequence can comprise all or a portion of an extracellular region of any transmembrane protein. In one embodiment, for example, the extracellular spacer sequence is derived from the human CD8α molecule or the human CD28 molecule.

The inventive CAR also comprises a transmembrane domain. The transmembrane domain can be any transmembrane domain derived or obtained from any molecule known in the art. For example, the transmembrane domain can be obtained or derived from a CD8α molecule or a CD28 molecule. CD8 is a transmembrane glycoprotein that serves as a co-receptor for the T-cell receptor (TCR), and is expressed primarily on the surface of cytotoxic T-cells. The most common form of CD8 exists as a dimer composed of a CD8α and CD8β chain. CD28 is expressed on T-cells and provides co-stimulatory signals required for T-cell activation. CD28 is the receptor for CD80 (B7.1) and CD86 (B7.2). In a preferred embodiment, the CD8α and CD28 are human.

The inventive CAR comprises a T-cell activation moiety. The T-cell activation moiety comprises at least one intracellular (i.e., cytoplasmic) T-cell signaling domain (also referred to as a "costimulatory domain"). The most common intracellular T-cell signaling domain employed in CARs is CD3 zeta (CD3ζ), which associates with TCRs to produce a signal and contains immunoreceptor tyrosine-based activation motifs (ITAMs). Preferably, the T-cell activation moiety comprises multiple (i.e., two or more) intracellular T-cell signaling domains. The intercellular T-cell signaling domains can be obtained or derived from a CD28 molecule, a CD3 zeta (ζ) molecule or modified versions thereof, the gamma chain of a human high-affinity IgE receptor (FcεRI), a CD27 molecule, an OX40 molecule, a 4-1BB molecule, or other intracellular signaling molecules known in the art. As discussed above, CD28 is a T-cell marker important in T-cell co-stimulation. 4-1BB, also known as CD137, transmits a potent costimulatory signal to T-cells, promoting differentiation and enhancing long-term survival of T lymphocytes. CD27 is a member of the TNF receptor superfamily, and is required for generation and long-term maintenance of T-cell immunity. The human high-affinity IgE receptor (FcεRI) is a tetrameric receptor complex consisting of one alpha, one beta, and two disulfide bridge connected gamma chains. FcεRI is constitutively expressed on mast cells and basophils and is inducible in eosinophils. In a preferred embodiment, the intracellular T-cell signaling domains are human.

The inventive CAR can comprise any one of aforementioned transmembrane domains and any one or more (e.g., 1, 2, 3, or 4) of the aforementioned intracellular T-cell signaling domains in any combination. For example, the inventive CAR can comprise a CD28 transmembrane domain and intracellular T-cell signaling domains of CD28 and CD3ζ. Alternatively, for example, the inventive Car can comprise a CD8α transmembrane domain and intracellular T-cell signaling domains of CD28, CD3ζ, the gamma chain of FcεRI, and/or 4-1BB. In another embodiment, the inventive CAR can comprise a CD8α transmembrane domain and intracellular T-cell signaling domains of CD28, CD3ζ, and CD27. In yet another embodiment, the inventive CAR can comprise a CD28 transmembrane domain and intracellular T-cell signaling domains of CD27, 4-1BB, and the gamma chain of FcεRI.

The invention further provides an isolated or purified nucleic acid sequence encoding the inventive chimeric antigen receptor (CAR). "Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides.

The inventive CAR can comprise any number of amino acids, provided that the CAR retains its biological activity, e.g., the ability to specifically bind to antigen, detect diseased cells in a mammal, or treat or prevent disease in a mammal, etc. For example, the CAR can comprise 50 or more (e.g., 60 or more, 100 or more, or 500 or more) amino acids, but less than 1,000 (e.g., 900 or less, 800 or less, 700 or less, or 600 or less) amino acids. Preferably, the CAR is about 50 to about 700 amino acids (e.g., about 70, about 80, about 90, about 150, about 200, about 300, about 400, about 550, or about 650 amino acids), about 100 to about 500 amino acids (e.g., about 125, about 175, about 225, about 250, about 275, about 325, about 350, about 375, about 425, about 450, or about 475 amino acids), or a range defined by any two of the foregoing values.

Included in the scope of the invention are functional portions of the inventive CAR described herein. The term "functional portion," when used in reference to a CAR, refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to a nucleic acid sequence encoding the parent CAR, a nucleic acid sequence encoding a functional portion of the CAR can encode a protein comprising, for example, about 10%, 25%, 30%, 50%, 68%, 80%, 90%, 95%, or more, of the parent CAR.

A functional portion of a CAR can contain additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity of the CAR, as compared to the biological activity of the parent CAR.

The invention also provides functional variants of the inventive CAR. The term "functional variant," as used herein, refers to a CAR, a polypeptide, or a protein having substantial or significant sequence identity or similarity to the inventive CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 80% identical, about 90% identical, about 95% identical, or about 99% identical to the nucleic acid sequence encoding the parent CAR.

A functional variant can, for example, comprise the amino acid sequence of the inventive CAR with at least one conservative amino acid substitution. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the same amino acid sub-group, for example, lysine for arginine and vice versa such that a positive charge may be maintained; glutamic acid for aspartic acid and vice versa such that a negative charge may be maintained; serine for threonine such that a free —OH can be maintained; and glutamine for asparagine such that a free —NH$_2$ can be maintained.

Alternatively or additionally, the functional variants can comprise the amino acid sequence of the parent CAR with at least one non-conservative amino acid substitution. "Non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution may enhance the biological activity of the functional variant, such that the biological activity of the functional variant is increased as compared to the parent CAR.

The inventive CAR (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The inventive CAR (including functional portions and functional variants thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The invention also provides a CAR directed to any target molecule of interest (i.e., comprises any antigen recognition moiety) that comprises any one of the aforementioned extracellular spacers, transmembrane domains, and intracellular T-cell signaling domains in any combination. For example, the inventive CAR can comprise (i) an extracellular spacer, (i) a transmembrane domain derived from a human CD8α molecule, and (iii) intracellular T-cell signaling domains derived from a human CD3 zeta (CD3ζ) molecule and a human CD28 molecule (as employed in the CAR of SEQ ID NO: 1). In another embodiment, the inventive CAR can comprise (i) an extracellular spacer, (i) a transmembrane domain derived from a human CD8α molecule, and (iii) intracellular T-cell signaling domains derived from a human CD28 molecule, a human CD27 molecule, and a human CD3ζ molecule (as employed in the CAR of SEQ ID NO: 4). In another embodiment, the inventive CAR can comprise (i) an extracellular spacer, (i) a transmembrane domain derived from a human CD8α molecule, and (iii) intracellular T-cell signaling domains derived from a human CD28 molecule, a human CD27 molecule, and the gamma chain of FcεRI (as employed in the CAR of SEQ ID NO: 10). In yet another embodiment, the inventive CAR can comprise (i) an extracellular spacer, (i) a transmembrane domain derived from a human CD8α molecule, and (iii) intracellular T-cell signaling domains derived from a human CD28 molecule and the gamma chain of Fc6RI (as employed in the CAR of SEQ ID NO: 12).

In a preferred embodiment, the inventive CAR comprises or consists of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

The inventive CAR can be generated using methods known in the art. For example, nucleic acid sequences, polypeptides, and proteins can be recombinantly produced using standard recombinant DNA methodology (see, e.g., Sambrook et al., *Molecular Cloning: A Laboratory Manual*, 3$^{rd}$ ed., Cold Spring Harbor Press, Cold Spring Harbor, N.Y., 2001; and Ausubel et al., *Current Protocols in Molecular Biology, Greene Publishing Associates and* John Wiley & Sons, N Y, 1994). Further, a synthetically produced nucleic acid sequence encoding the CAR can be isolated and/or purified from a source, such as a plant, a bacterium, an insect, or a mammal, e.g., a rat, a human, etc. Methods of isolation and purification are well-known in the art. Alternatively, the nucleic acid sequences described herein can be commercially synthesized. In this respect, the nucleic acid sequence can be synthetic, recombinant, isolated, and/or purified.

The invention also provides a vector comprising the nucleic acid sequence encoding the inventive CAR. The vector can be, for example, a plasmid, a cosmid, a viral vector (e.g., retroviral or adenoviral), or a phage. Suitable vectors and methods of vector preparation are well known in the art (see, e.g., Sambrook et al., supra, and Ausubel et al., supra).

In addition to the nucleic acid sequence encoding the inventive CAR, the vector preferably comprises expression control sequences, such as promoters, enhancers, polyadenylation signals, transcription terminators, internal ribosome entry sites (IRES), and the like, that provide for the expression of the nucleic acid sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, Calif.), LACSWITCH™ System (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), *Fundamental Immunology*, 3rd Edition, Raven Press, New York (1993), pages 353-363; and U.S. Pat. No. 5,885,827).

The vector also can comprise a "selectable marker gene." The term "selectable marker gene," as used herein, refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., *Proc. Natl. Acad. Sci. USA*, 77: 3567 (1980); O'Hare et al., *Proc. Natl. Acad. Sci. USA*, 78: 1527 (1981); Mulligan & Berg, *Proc. Natl. Acad. Sci. USA*, 78: 2072 (1981); Colberre-Garapin et al., *J. Mol. Biol.*, 150: 1 (1981); Santerre et al., *Gene*, 30: 147 (1984); Kent et al., *Science*, 237: 901-903 (1987); Wigler et al., *Cell*, 11: 223 (1977); Szybalska & Szybalski, *Proc. Natl. Acad. Sci. USA*, 48: 2026 (1962); Lowy et al., *Cell*, 22: 817 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.).

Viral vectors also can be used. Representative viral expression vectors include, but are not limited to, the adenovirus-based vectors (e.g., the adenovirus-based Per.C6 system available from Crucell, Inc. (Leiden, The Netherlands)), lentivirus-based vectors (e.g., the lentiviral-based pLP1 from Life Technologies (Carlsbad, Calif.)), and retroviral vectors (e.g., the pFB-ERV plus pCFB-EGSH from Stratagene (La Jolla, Calif.)). In a preferred embodiment, the viral vector is a lentivirus vector.

The vector comprising a nucleic acid encoding the inventive CAR can be introduced into a host cell that is capable of expressing the CAR, including any suitable prokaryotic or eukaryotic cell. Preferred host cells are those that can be easily and reliably grown, have reasonably fast growth rates, have well characterized expression systems, and can be transformed or transfected easily and efficiently.

As used herein, the term "host cell" refers to any type of cell that can contain the expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell can be a mammalian cell. The host cell preferably is a human cell. The host cell can be of any cell type, can originate from any type of tissue, and can be of any developmental stage. In one embodiment, the host cell can be a peripheral blood lymphocyte (PBL), a peripheral blood mononuclear cell (PBMC), a natural killer (NK), or a T-cell. Preferably, the host cell is a T-cell. Methods for selecting suitable mammalian host cells and methods for transformation, culture, amplification, screening, and purification of cells are known in the art.

The invention provides an isolated T-cell which expresses a nucleic acid sequence encoding the inventive CAR described herein. The T-cell of the invention can be any T-cell, such as a cultured T-cell, e.g., a primary T-cell, or a T-cell from a cultured T-cell line, or a T-cell obtained from a mammal. If obtained from a mammal, the T-cell can be obtained from numerous sources, including but not limited to blood, bone marrow, lymph node, the thymus, or other tissues or fluids. T-cells can also be enriched for or purified. The T-cell preferably is a human T-cell (e.g., isolated from a human). The T-cell can be of any developmental stage, including but not limited to, a $CD4^+/CD8^+$ double positive T-cell, a $CD4^+$ helper T-cell, e.g., $Th_1$ and $Th_2$ cells, a $CD8^+$ T-cell (e.g., a cytotoxic T-cell), a tumor infiltrating cell, a memory T-cell, a naïve T-cell, and the like. In one embodiment, the T-cell is a $CD8^+$ T-cell or a $CD4^+$ T-cell. T-cell lines are available from, e.g., the American Type Culture Collection (ATCC, Manassas, Va.), and the German Collection of Microorganisms and Cell Cultures (DSMZ) and include, for example, Jurkat cells (ATCC TIB-152), Sup-T1 cells (ATCC CRL-1942), RPMI 8402 cells (DSMZ ACC-290), Karpas 45 cells (DSMZ ACC-545), and derivatives thereof.

A nucleic acid sequence encoding the inventive CAR may be introduced into a cell by "transfection," "transformation," or "transduction." The terms "transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology*, Vol. 7, Gene Transfer and Expression Protocols, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al., *Mol. Cell Biol.*, 7: 2031-2034 (1987)). Phage or viral vectors can be introduced into host cells, after growth of infectious particles in suitable packaging cells, many of which are commercially available.

Without being bound to a particular theory or mechanism, it is believed that by eliciting an antigen-specific response against CD19, the inventive CARs provide for one or more of the following: targeting and destroying CD19-expressing cancer cells, reducing or eliminating cancer cells, facilitating infiltration of immune cells to tumor site(s), and enhancing/ extending anti-cancer responses. Thus, the invention provides a method of destroying malignant B-cells, which comprises contacting one or more of the aforementioned isolated T-cells with a population of malignant B-cells that express CD19, whereby the CAR is produced and binds to CD19 on the malignant B-cells and the malignant B-cells are destroyed. As discussed above, treatment of B-cell malignancies typically involves chemotherapy, therapeutic monoclonal antibodies, and allogeneic stem cell transplantation; however, a high rate of relapse is common in patients that have undergone such treatment. As discussed above, CD19 is highly expressed by malignant B-cells (see, e.g., Nadler et al., supra), and the inventive method can be used to treat any B-cell malignancy known in the art. Malignancies of mature B-cells include, but are not limited to, follicular lymphoma, mantle-cell lymphoma, Burkitt lymphoma, multiple myeloma, diffuse large B-cell lymphoma, Hodgkin lymphoma, lymphoplasmacytic lymphoma, marginal-zone lymphoma, and chronic lymphocytic leukemia (Shaffer et al., supra).

One or more isolated T-cells expressing a nucleic acid sequence encoding an inventive anti-CD19 CAR described herein can be contacted with a population of malignant B-cells that express CD19 ex vivo, in vivo, or in vitro. "Ex vivo" refers to methods conducted within or on cells or tissue in an artificial environment outside an organism with minimum alteration of natural conditions. In contrast, the term "in vivo" refers to a method that is conducted within living organisms in their normal, intact state, while an "in vitro" method is conducted using components of an organism that have been isolated from its usual biological context. The inventive method preferably involves ex vivo and in vivo components. In this regard, for example, the isolated T-cells described above can be cultured ex vivo under conditions to express a nucleic acid sequence encoding the inventive anti-CD19 CAR, and then directly transferred into a mammal (preferably a human) affected by a B-cell malignancy. Such a cell transfer method is referred to in the art as "adoptive cell transfer (ACT)," in which immune-derived cells are passively transferred into a new recipient host to transfer the functionality of the donor immune-derived cells to the new host. Adoptive cell transfer methods to treat various types of cancers, including hematological cancers such as B-cell malignancies, are known in the art and disclosed in, for example, Gattinoni et al., *Nat. Rev. Immunol.*, 6(5): 383-393 (2006); June, C H, *J. Clin. Invest.*, 117(6): 1466-76 (2007); Rapoport et al., *Blood*, 117(3): 788-797 (2011); and Barber et al., *Gene Therapy*, 18: 509-516 (2011)).

When T-cells are administered to a mammal, the cells can be allogeneic or autologous to the mammal. In "autologous" administration methods, cells (e.g., blood-forming stem cells or lymphocytes) are removed from a mammal, stored (and optionally modified), and returned back to the same mammal. In "allogeneic" administration methods, a mammal receives cells (e.g., blood-forming stem cells or lymphocytes) from a genetically similar, but not identical, donor. Preferably, the cells are autologous to the mammal.

The T-cells desirably are administered to a human in the form of a composition, such as a pharmaceutical composition. Alternatively, a nucleic acid sequence encoding the inventive CAR, or a vector comprising the CAR-encoding nucleic acid sequence, can be formulated into a composition, such as a pharmaceutical composition, and administered to a human. The inventive pharmaceutical composition can comprise a population of T-cells that expresses the inventive CAR. In addition to a nucleic acid sequence encoding the inventive CAR, or host cells which express the inventive CAR, the pharmaceutical composition can comprise other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises an isolated T-cell which expresses the inventive CAR, more preferably a population of T-cells which expresses the inventive CAR.

The inventive T-cells can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The choice of carrier will be determined in part by the particular inventive CAR, CAR-encoding nucleic acid sequence, vector, or host cells expressing the CAR, as well as by the particular method used to administer the inventive CAR, CAR-encoding nucleic acid sequence, vector, or host cells expressing the CAR. Accordingly, there are a variety of suitable formulations of the pharmaceutical composition of the invention. For example, the pharmaceutical composition can contain preservatives. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

In addition, buffering agents may be used in the composition. Suitable buffering agents include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

Methods for preparing administrable (e.g., parenterally administrable) compositions are known to those skilled in the art and are described in more detail in, for example, *Remington: The Science and Practice of Pharmacy*, Lippincott Williams & Wilkins; 21st ed. (2005).

The composition comprising the inventive CAR, CAR-encoding nucleic acid sequence, vector or host cells expressing the CAR, can be formulated as an inclusion complex, such as cyclodextrin inclusion complex, or as a liposome. Liposomes can serve to target the host cells (e.g., T-cells or NK cells) or the inventive nucleic acid sequence to a particular tissue. Liposomes also can be used to increase the half-life of the inventive nucleic acid sequence. Many methods are available for preparing liposomes, such as those described in, for example, Szoka et al., *Ann. Rev. Biophys. Bioeng.*, 9: 467 (1980), and U.S. Pat. Nos. 4,235,871, 4,501,728, 4,837,028, and 5,019,369.

The composition can employ time-released, delayed release, and sustained release delivery systems such that the delivery of the inventive composition occurs prior to, and with sufficient time to cause, sensitization of the site to be treated. Many types of release delivery systems are available and known to those of ordinary skill in the art. Such systems can avoid repeated administrations of the composition, thereby increasing convenience to the subject and the physician, and may be particularly suitable for certain composition embodiments of the invention.

The composition desirably comprises the host cells expressing a nucleic acid sequence encoding the inventive CAR, or a vector comprising such a nucleic acid sequence, in an amount that is effective to treat or prevent a B-cell malignancy. As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the composition comprising the host cells expressing the inventive CAR, or a vector comprising a CAR-encoding nucleic acid sequence. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the CAR to elicit a desired response in the individual. For example, a therapeutically effective amount of CAR of the invention is an amount which binds to CD19 on multiple myeloma cells and destroys them.

Alternatively, the pharmacologic and/or physiologic effect may be prophylactic, i.e., the effect completely or partially prevents a disease or symptom thereof. In this respect, the inventive method comprises administering a "prophylactically effective amount" of the composition comprising the host cells expressing the inventive CAR, or a vector comprising a CAR-encoding nucleic acid sequence, to a mammal that is predisposed to a B-cell malignancy. A "prophylactically effective amount" refers to an amount effective, at dosages and for periods of time necessary, to achieve a desired prophylactic result (e.g., prevention of disease onset).

A typical amount of host cells administered to a mammal (e.g., a human) can be, for example, in the range of one million to 100 billion cells; however, amounts below or above this exemplary range are within the scope of the invention. For example, the daily dose of inventive host cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), preferably about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), more preferably about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising the host cells expressing the inventive CAR, or a vector comprising a CAR-encoding nucleic acid sequence, can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

The composition comprising the host cells expressing the inventive CAR, or a vector comprising a CAR-encoding nucleic acid sequence, can be administered with one or more additional therapeutic agents, which can be coadministered to the mammal. By "coadministering" is meant administering one or more additional therapeutic agents and the composition comprising the inventive host cells or the inventive vector sufficiently close in time such that the inventive CAR can enhance the effect of one or more additional therapeutic agents, or vice versa. In this regard, the composition comprising the inventive host cells or the inventive vector can be administered first, and the one or more additional therapeutic agents can be administered second, or vice versa. Alternatively, the composition comprising the inventive host cells or the inventive vector and the one or more additional therapeutic agents can be administered simultaneously. An example of a therapeutic agent that can be co-administered with the composition comprising the inventive host cells or the inventive vector is IL-2.

Once the composition comprising host cells expressing the inventive CAR, or a vector comprising a CAR-encoding nucleic acid sequence, is administered to a mammal (e.g., a human), the biological activity of the CAR can be measured by any suitable method known in the art. In accordance with the inventive method, the CAR binds to CD19 on malignant B-cells, and the malignant B-cells are destroyed. Binding of the CAR to CD19 on the surface malignant B-cells can be assayed using any suitable method known in the art, including, for example, ELISA and flow cytometry. The ability of the CAR to destroy malignant B-cells can be measured using any suitable method known in the art, such as cytotoxicity assays described in, for example, Kochenderfer et al., *J. Immunotherapy*, 32(7): 689-702 (2009), and Herman et al. *J. Immunological Methods*, 285(1): 25-40 (2004). The biological activity of the CAR also can be measured by assaying expression of certain cytokines, such as CD107a, IFNγ, IL-2, and TNF.

One of ordinary skill in the art will readily appreciate that the inventive CAR can be modified in any number of ways, such that the therapeutic or prophylactic efficacy of the CAR is increased through the modification. For instance, the CAR can be conjugated either directly or indirectly through a linker to a targeting moiety. The practice of conjugating compounds, e.g., the CAR, to targeting moieties is known in the art. See, for instance, Wadwa et al., *J Drug Targeting* 3: 111 (1995), and U.S. Pat. No. 5,087,616.

The following examples further illustrate the invention but, of course, should not be construed as in any way limiting its scope.

Example 1

This example demonstrates methods for generating the inventive anti-CD19 chimeric antigen receptors (CARs).

A series of anti-CD19 CARs were designed and synthesized. All of the CARs contained an antigen-recognition domain comprised of a single chain variable fragment (scFv) derived from either the murine monoclonal antibody FMC63 (Nicholson et al., *Molecular Immunology*, 34(16-17): 1157-1165 (1997)) or the fully human monoclonal antibody 47G4 (U.S Patent Application Publication No. 2010/0104509). The CARs comprised a signal sequence from the human granulocyte-macrophage colony stimulating factor (GM-CSF) receptor, or a signal sequence from the human CD8 molecule. The CARs contained a combination of two or more intracellular T-cell signaling domains (or "costimulatory domains") derived from the human CD3 zeta (CD3ζ) molecule, the human CD28 molecule, the human 4-1BB molecule, the human CD27 molecule, and/or the gamma chain of FcεRI.

More specifically, a plasmid denoted FMC63-CD828Z, which encodes a CAR comprising an FMC63-derived scFv, a GM-CSF-receptor signal sequence, CD8 extracellular and transmembrane components, and intracellular T-cell signaling domains of the human CD3 and CD28 molecules was constructed using the plasmid MSGV-FMC63-28Z (described in Kochenderfer et al., *Journal of Immunotherapy*, 32(7): 689-702 (2009)) as the staring material. The MSGV-FMC63-28Z plasmid was first cleaved with the restriction enzymes NotI and BmgBI (New England Biolabs, Ipswich, Mass.), which eliminated the entire CD28 portion of this plasmid. Next, a DNA fragment (synthesized by Invitrogen, Carlsbad, Calif.) encoding part of the extracellular region and all of the transmembrane region of the human CD8 molecule, the cytoplasmic portion of the CD28 molecule, and the cytoplasmic part of the CD3 molecule was ligated into the cleaved MSGV-FMC63-28Z plasmid. The sequences of human CD8, CD28, and CD3 were obtained from the National Center for Biotechnology Information website. Guidance regarding the portions of each molecule to include in the CARs was obtained from Kochenderfer et al., *Journal of Immunotherapy*, 32(7): 689-702 (2009).

Fully human anti-CD19 CARs were generated by utilizing sequences of the fully human 47G4 monoclonal antibody (described in U.S Patent Application Publication No. 2010/0104509). The 47G4 antibody was generated by vaccinating mice of the KM strain, which carry a human kappa light chain transgene and a human heavy chain transchromosome. The sequences of the 47G4 antibody light chain and heavy chain variable regions were obtained from U.S Patent Application Publication No. 2010/0104509. A 47G4 scFv was designed comprising the following elements from 5' to 3': a CD8 signal sequence, the 47G4 antibody light chain variable region, a linker peptide comprising the amino acid sequence GSTSGSGKPGSGEGSTKG (SEQ ID NO: 14) (see Cooper et al., *Blood*, 101(4): 1637-1644 (2003)), and the 47G4 antibody heavy chain variable region. A DNA sequence encoding a CAR was then designed comprising the following components from 5' to 3': the 47G4 scFv described above, part of the extracellular region and all of the transmembrane region of the human CD8 molecule, and the cytoplasmic portions of the human CD28 molecule and the human CD3ζ molecule. This CAR was designated 47G4-CD828Z, and the sequence was synthesized by Invitrogen (Carlsbad, Calif.).

Using standard methods, the pRRLSIN.cPPT.MSCV.coDMF5.oPRE lentiviral plasmid (described in Yang et al., *Journal of Immunotherapy*, 33(6): 648-658 (2010)) was modified to replace the coDMF5 portion of the plasmid with the 47G4-CD828Z CAR sequence described above. The resulting plasmid was denoted LSIN-47G4-CD8CD28Z.

A plasmid designated MSGV-47G4-CD8BBZ was constructed by modifying the above-described MSGV-FMC63-CD828Z plasmid using standard methods. The MSGV-47G4-CD8BBZ plasmid encodes a CAR designated 47G4-CD8BBZ comprising, from 5' to 3': the 47G4 scFv described above, part of the extracellular region and all of the transmembrane region of the human CD8 molecule, a portion of the human 4-1BB (CD137) molecule comprising the amino acid sequence RFSVVKRGRKKLLY-IFKQPFMRPVQTTQEEDGCSCRFPEEEEGGCEL (SEQ ID NO: 15), and the cytoplasmic portion of the CD3 molecule.

A plasmid designated MSGV-FMC63-CD8BBZ encoding a CAR designated FMC63-CD8BBZ CAR was constructed by replacing the CD28 sequence of the plasmid MSGV-FMC63-CD828Z with the same 4-1BB sequence included in MSGV-47G4-CD8BBZ.

DNA encoding an SP6 scFv (Ochi et al., *Proc. Natl. Acad. Sci. USA*, 80(20):6351-6355 (1983)) was ligated into the MSGV-FMC63-CD828Z retroviral vector after excision of DNA encoding the FMC63 scFv to form the MSGV-SP6-CD828Z, which recognized the hapten 2, 4, 6-trinitrobenzenesulfonic acid and served as a negative control in some experiments.

All of the anti-CD19 CARs generated using the methods described above are set forth in Table 1.

TABLE 1

| anti-CD19 CAR | Amino Acid SEQ ID NO | Signal Sequence | Extracellular and Transmembrane Regions | Intracellular T-cell Signaling Domain |
|---|---|---|---|---|
| 47G4-CD828Z | 1 | Human CD8α | Human CD8α | CD28 CD3ζ |
| 47G4-CD8BBZ | 2 | Human CD8α | Human CD8α | 4-1BB CD3ζ |
| 47G4-CD827Z | 3 | Human CD8α | Human CD8α | CD27 CD3ζ |
| 47G4-CD82827Z | 4 | Human CD8α | Human CD8α | CD28 CD27 CD3ζ |
| 47G4-CD827BBZ | 5 | Human CD8α | Human CD8α | 4-1BB CD27 CD3ζ |
| FMC63-CD828Z | 6 | GM-CSF receptor | Human CD8α | CD28 CD3ζ |

TABLE 1-continued

| anti-CD19 CAR | Amino Acid SEQ ID NO | Signal Sequence | Extracellular and Transmembrane Regions | Intracellular T-cell Signaling Domain |
|---|---|---|---|---|
| FMC63-CD827BBZ | 7 | GM-CSF receptor | Human CD8α | CD27<br>4-1BB<br>CD3ζ |
| FMC63-CD827Z | 8 | GM-CSF receptor | Human CD8α | CD27<br>CD3ζ |
| FMC63-CD82827Z | 9 | GM-CSF receptor | Human CD8α | CD28<br>CD27<br>CD3ζ |
| 47G4-CD82827GAMMA | 10 | Human CD8α | Human CD8α | CD28<br>CD27<br>FcεRI gamma chain |
| FMC63-CD82827GAMMA | 11 | Human CD8α | Human CD8α | CD28<br>CD27<br>FcεRI gamma chain |
| 47G4-CD828GAMMA | 12 | Human CD8α | Human CD8α | CD28<br>FcεRI gamma chain |
| FMC63-CD828GAMMA | 13 | GM-CSF receptor | Human CD8α | CD28<br>FcεRI gamma chain |

The results of this example demonstrate the generation of anti-CD19 CARs based on a fully human monoclonal anti-CD19 antibody and a murine monoclonal anti-CD19 antibody.

Example 2

This example demonstrates a method of generating T-cells expressing nucleic acid sequences encoding the inventive CARs.

Replication incompetent gammaretroviruses or lentiviruses encoding the above-described CARs were produced and used to transduce T-cells. To transiently produce replication-incompetent gammaretroviruses, 293GP packaging cells (Burns et al., *Proc. Natl. Acad. Sci., USA*, 90(17): 8033-8037 (1993)) were transfected with plasmids encoding the CARs described in Example 1 along with a plasmid encoding the RD114 envelope protein (Porter et al., *Human Gene Therapy*, 7(8): 913-919 (1996)) using LIPOFECTAMINE™ 2000 (Life Technologies, Carlsbad, Calif.). The transfected cells were incubated at 37° C. for 6-8 hours in D10 medium without antibiotics. The medium used for transfection was then replaced with fresh D10 medium and the cells were incubated for another 36-48 hours. During and after transfection, the 293GP cells were cultured on poly-D-lysine coated dishes (BD Biosciences, San Jose, Calif.). Supernatant containing retroviruses was removed from the dishes and centrifuged to remove cellular debris. The supernatant was stored at −80° C.

Supernatant that contained lentiviruses encoding each of the CARs described in Example 1 was produced using the protocol described in Yang et al., *Journal of Immunotherapy*, 33(6): 648-658 (2010)).

Peripheral blood mononuclear cells (PBMC) were thawed and washed once in T-cell medium. PBMC were suspended at a concentration of 1×10⁶ cells/mL in T-cell medium containing 50 ng/mL of the anti-CD3 monoclonal antibody OKT3 (Ortho, Bridgewater, N.J.) and 300 IU/mL of IL-2. Twenty mL of this suspension were added to 75 cm² culture flasks (Corning, Corning, N.Y.). The flasks were cultured upright at 37° C. and 5% CO₂ (see, e.g., Kochenderfer et al., *Journal of Immunotherapy*, 32(7): 689-702 (2009)).

Gammaretroviral transduction of T-cells was carried out by first dissolving RETRONECTIN™ (Takara/Clontech Laboratories, Mountain View, Calif.) at a concentration of 10 g/mL in PBS, and two mL of this RetroNectin™ in PBS solution were added to each well of nontissue-culturecoated 6 well plates (BD Biosciences). The plates were incubated for 2 hours at room temperature (RT). After the incubation, the RETRONECTIN™ solution was aspirated and 2 mL of a blocking solution consisting of Hanks' balanced salt solution (HBSS) plus 2% bovine serum albumin (BSA) were added to each RETRONECTIN™-coated well. The plates were incubated for 30 minutes at room temperature. The blocking solution was aspirated, and the wells were rinsed with a solution of HBSS+2.5% HEPES. Gammaretroviral supernatant was rapidly thawed and diluted 1:1 in T-cell media. Two mL of the diluted supernatant were then added to each RETRONECTIN™-coated well.

After addition of the supernatants, the plates were centrifuged at 2000×g for 2 hours at 32° C. The supernatant was then aspirated from the wells, and 2×10⁶ T-cells cultured with OKT3 and IL-2 for 2 days were added to each well. When the T-cells were added to the retrovirus-coated plates, they were suspended at a concentration of 0.5×10⁶ cells per mL in T-cell medium plus 300 IU/mL of IL-2. After the T-cells were added to each well, the plates were centrifuged for 10 minutes at 1000×g and incubated overnight at 37° C. After a 24-30 hour incubation, the T-cells were removed from the plates and suspended in fresh T-cell medium with 300 IU/mL of IL-2 at a concentration of 0.5×10⁶ cells per mL and cultured at 37° C. and 5% CO₂.

For lentiviral transduction of T-cells, activated PBMC were suspended in lentiviral supernatant with protamine sulfate and 300 IU/mL IL-2. The cells were centrifuged for 1 hour at 1200×g. The cells were then cultured for 3 hours at 37° C. Next, the supernatant was diluted 1:1 with RPMI (Mediatech, Inc., Manassas, Va.)+10% fetal bovine serum (Invitrogen, Carlsbad, Calif.) and IL-2. The cells were cultured in the diluted supernatant overnight and then they were returned to culture in AIM V medium plus 5% human AB serum with IL-2.

Expression of the FMC63-based CARs on transduced T-cells was assessed. Specifically, transduced T-cells were washed and suspended in FACs buffer (Phosphate-buffered saline (PBS) plus 0.1% sodium azide and 0.4% BSA). Biotin-labeled polyclonal goat anti-mouse F(ab)2 antibodies (anti-Fab, Jackson Immunoresearch, West Grove, Pa.) were added to detect the FMC63 scFv. The cells were incubated at 4° C. for 25 minutes and washed once. The cells were suspended in FACs buffer and blocked with normal mouse IgG (Invitrogen, Carlsbad, Calif.). The cells were then stained with phycoerythrin (PE)-labeled streptavidin (BD Pharmingen, San Diego, Calif.), anti-CD4, anti-CD8, and anti-CD3. Flow cytometry acquisition was performed with a LSR II flow cytometer (BD Biosciences), and analysis was performed with FlowJo software (Treestar, Inc. Ashland, Oreg.). Expression of the 47G4-based CARs on transduced T-cells was assessed using a nearly identical method, except that Biotin-labeled protein L (GenScript, Piscataway, N.J.) was used instead of the Biotin-labeled polyclonal goat anti-mouse-F(ab)2 antibodies.

The percentage of CAR-expressing (CAR+) T-cells was calculated as the percentage of T-cells in CAR-transduced cultures that stained with the anti-Fab antibodies or protein L minus the percentage of identically-cultured untransduced T-cells from the same donor that stained with anti-Fab or protein L in each experiment.

Figure 1:
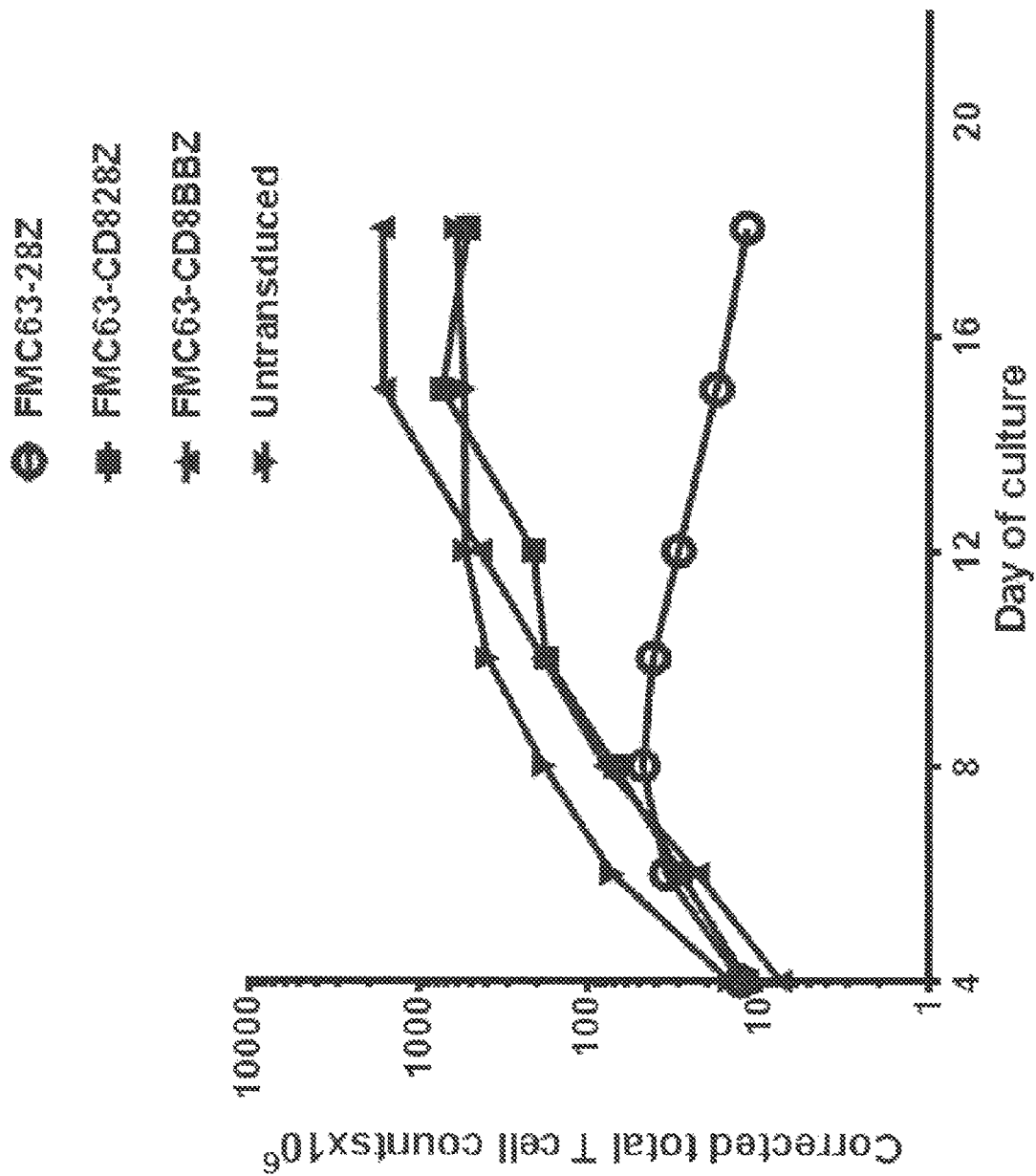

On day 7 of culture, the percentages of T-cells expressing CARs comprising an scFv derived from the murine FMC63 antibody were as follows: FMC63-28Z, 71%; FMC63-CD828Z, 88%; and FMC63-CD8BBZ, 87%. FMC63-28Z CAR expressing T-cells exhibited shorter in vitro survival as compared to T-cells expressing the FMC63-CD828Z CAR or the FMC63-CD8BB CAR in IL-2-containing cultures, as shown in FIG. 1. High levels of CAR expression also were detected on T-cells transduced with gammaretroviruses encoding FMC63-CD828Z, FMC63-CD8BBZ, and FMC63-CD827Z.

CARs comprising a scFv derived from the 47G4 antibody were expressed at high levels on the surface of human T-cells. In particular, FIGS. 2A-2D show the expression of 47G4-based CARs comprising the CD27 intracellular signaling domain, while FIGS. 3A and 3B show expression of the 47G4-CD828Z CAR.

The results of this example demonstrate that T-cells can be engineered to express the inventive anti-CD19 CARs.

Example 3

This example describes a series of experiments used to determine the specificity of the inventive CARs for CD19.
Patient Samples and Cell Lines Non-leukemic PBMC samples were obtained from melanoma, chronic lymphocytic leukemia (CLL), or lymphoma patients who were enrolled on institutional review board approved protocols in the Surgery Branch of the National Cancer Institute (NCI). Cells from 5 different patients were used. Donor 1 had CLL, Donor 2 was a normal donor, Donor 3 and Donor 5 both had lymphoma, and Donor 4 had melanoma. PBMC were cryopreserved in 90% FBS plus 10% DMSO (Sigma, St. Louis, Mo.). In experiments that used primary CLL cells as target cells, unmanipulated PBMC from patients with CLL were used. The following CD19-expressing immortalized cell lines were used: NALM-6 (acute lymphoid leukemia from DSMZ, Braunschweig, Germany), and CD19-K562. The following CD19-negative cell lines were used: A549 (lung carcinoma, from ATCC), CCRF-CEM (T-cell leukemia from ATCC), MDA231 (breast carcinoma from ATCC), and TC71 (Ewing's sarcoma, a kind gift of Dr. M. Tsokos, National Cancer Institute, Bethesda, Md.). All cell lines were maintained in R10 medium. When CLL PBMC were used as targets in assays, the cells were cultured in R10 medium for 12-18 hours prior to the assay.

Interferon- and TNF Enzyme-Linked Immunosorbent Assays (ELISA)

The occurrence of hypotension and other toxicities in patients receiving infusions of T-cells expressing the CAR FMC63-28Z in clinical trials prompted a comparison of TNF production by T-cells expressing FMC63-28Z to TNF production by T-cells expressing the inventive CARs.

Target cells were washed and suspended at $1\times10^6$ cells per mL in T-cell media without IL-2. 100,000 target cells of each target cell type were added to each of two wells of a 96 well round bottom plate (Corning, Tewksbury, Mass.). Wells containing T-cells alone also were prepared. The plates were incubated at 37° C. for 18-20 hours. Following the incubation, an IFNγ or a TNF ELISA assay was performed using standard methods (Pierce, Rockford, Ill.). In some experiments TNF ELISA results were normalized by dividing the TNF levels by the percentage of T-cells in the overnight cultures expressing a given CAR. CAR expression was determined as described in Example 2.

When normalized for cell-surface CAR expression, T-cells expressing FMC63-28Z consistently produced more TNF than the FMC-CD828Z CAR and the FMC63-CD8BBZ CAR, as show in FIGS. 4A and 4B. The only difference between the FMC63-28Z CAR and the FMC63-CD828Z CAR is the replacement of the human CD28 extracellular and transmembrane components of FMC63-28Z with extracellular and transmembrane components from the human CD8 protein in FMC63-CD828Z. The marked difference in T-cell persistence and inflammatory cytokine production between FMC63-28Z and FMC63-CD828Z led to the use of the CD8 extracellular spacer and transmembrane components in subsequent CAR designs.

T-cells transduced with the anti-CD19 CARs produced large amounts of IFNγ when they were cultured overnight with the CD19-expressing cell line CD19-K562, but the CAR-transduced T-cells only produced background levels of IFNγ when they were cultured with the negative control cell line lines, as indicated in Tables 2 and 3 (all units are pg/mL IFNγ). The results of the IFNγ ELISA for the 47G4-CD828Z CAR are shown in FIG. 5.

TABLE 2

| Effector Cells | CD19-Positive Targets | | CD19-Negative Targets | | | T-Cells Alone | % of CAR + T-cells |
|---|---|---|---|---|---|---|---|
| | CD19-K562 | CLL | NGFR-K562 | CEM | A549 | | |
| 47G4-CD8BBZ | 33926 | 10498 | 5885 | 6342 | 8188 | 5300 | 90 |
| FMC63-CD8BBZ | 44327 | 13919 | 4211 | 4405 | 5407 | 4003 | 86 |
| Untransduced | <12 | 1060 | 16 | <12 | <12 | | 0 |

TABLE 3

| Effector Cells | CD19-Positive Targets | | CD19-Negative Targets | | T-Cells Alone |
|---|---|---|---|---|---|
| | CD19-K562 | CLL | NGFR-K562 | MDA231 | |
| 47G4-CD827Z | 7435 | 1833 | 39 | 87 | 37 |
| 47G4-CD828Z | 13819 | 1300 | 22 | 45 | 16 |
| 47G4-CD828GAMMA | 9963 | 866 | 19 | 30 | <12 |

TABLE 3-continued

| Effector Cells | CD19-Positive Targets | | CD19-Negative Targets | | T-Cells Alone |
| --- | --- | --- | --- | --- | --- |
| | CD19-K562 | CLL | NGFR-K562 | MDA231 | |
| 47G4-CD82827Z | 11874 | 2436 | 32 | 68 | 27 |
| 47G4-CD82827GAMMA | 8351 | 870 | 23 | 46 | 18 |
| 47G4-CD8BBZ | 13381 | 2394 | 87 | 175 | 82 |
| Untransduced | 18 | 16 | 16 | 32 | <12 |

High background IFNγ secretion was a consistent observation with CARs containing a 4-1BB moiety. T-cells transduced with the FMC63-CD827Z CAR produced IFNγ in a CD19-specific manner. Much lower levels of IFNγ were elicited when the FMC63-CD827Z cells were cultured with NGFR-K562 and CCRF-CEM cells, which are CD19-negative. FMC63-CD827Z-transduced T-cells also produced TNF in an antigen-specific manner.

CD107a Assay

For each T-cell culture that was tested, two or three separate tubes were prepared. One tube contained CD19-K562 cells, one tube contained unmanipulated primary CLL cells, and the other tube contained NGFR-K562 cells. In some experiments, the CD19-K562 tube was omitted. All tubes contained T-cells transduced with the anti-CD19 CARs described above, 1 mL of AIM V™ medium (Life Technologies, Carlsbad, Calif.)+5% human serum, a titrated concentration of an anti-CD107a antibody (eBioscience, Inc., San Diego, Calif.; clone eBioH4A3), and 1 µL of Golgi Stop (BD Biosciences, Franklin Lakes, N.J.). All tubes were incubated at 37° C. for four hours and then stained for expression of CD3, CD4, and CD8.

T-cells from different subjects expressing the CARs FMC63-CD828Z, FMC63-CD827Z, FMC63-CD8BBZ, 47G4-CD827Z, 47G4-CD82827Z, 47G4-CD827BBZ, or 47G4-CD8BBZ upregulated CD107a specifically in response to stimulation with CD19-expressing target cells, and the results of the CD107a assay for the 47G4-CD827Z, 47G4-CD82827Z, 47G4-CD827BBZ CARs are shown in FIGS. 6A-6D. This indicates the occurrence of CD19-specific degranulation of the T-cells, which is a prerequisite for perforin-mediated cytotoxicity (see, e.g., Rubio et al., *Nature Medicine*, 9(11): 1377-1382 (2003)).

Proliferation Assays

The ability of T-cells transduced with the anti-CD19 CARs to proliferate when stimulated with CD19-expressing target cells was assessed. Specifically, 0.5×10⁶ irradiated irradiated CD19-K562 cells or 0.5×10⁶ irradiated NGFR-K562 cells were co-cultured with 0.75×10⁶ total T-cells transduced with an anti-CD19 CAR. The T-cells were labeled with carboxyfluorescein diacetate succinimidyl ester (CFSE) (Life Technologies, Carlsbad, Calif.) as described in Mannering et al., *J. Immunological Methods*, 283(1-2): 173-183 (2003). The medium used in the co-cultures was AIM V™ medium (Life Technologies, Carlsbad, Calif.)+5% human AB serum. IL-2 was not added to the medium. Four days after initiation, the live cells in each co-culture were counted with trypan blue for dead cell exclusion, and flow cytometry was performed as described in Example 2

T-cells expressing the CARs FMC63-CD8BBZ, FMC63-CD828Z, and 47G4-CD8BBZ, all exhibited a greater dilution of CFSE when cultured with the CD19-K562 cells than when cultured with negative control NGFR-K562 cells, as shown in FIGS. 7A-7C. These results indicate that T-cells transduced with the anti-CD19 CARs specifically proliferated when stimulated with CD19-expressing target cells.

The results of this example demonstrate that T-cells expressing the inventive CARs exhibit CD19-specific cytokine production, degranulation, and proliferation.

Example 4

This example demonstrates that T-cells expressing an inventive anti-CD19 CAR can destroy chronic lymphocytic leukemia (CLL) cells.

Cytotoxicity assays were performed to determine whether T-cells transduced with the inventive FMC63-CD828Z CAR could destroy CD19-expressing unmanipulated PBMC from patients with CLL. Specifically, the cytotoxicity of target cells was measured by comparing the survival of CD19-expressing target cells (i.e., CLL PBMC) relative to the survival of negative control CCRF-CEM cells using an assay described in, e.g., Kochenderfer et al., *J. Immunotherapy*, 32(7): 689-702 (2009), and Hermans et al., *J. Immunological Methods*, 285(1): 25-40 (2004).

CCRF-CEM cells were suspended in R10 medium at a concentration of 1.5×10⁶ cells/mL, and the fluorescent dye 5-(and -6)-(((4-chloromethyl)benzoyl)amino) tetramethylrhodamine (CMTMR) (Life Technologies, Carlsbad, Calif.) was added at a concentration of 5 M. The cells were mixed and then incubated at 37° C. for 30 minutes. The cells were then washed, suspended in cytotoxicity medium, and incubated at 37° C. for 60 minutes. The cells were then washed twice and suspended in cytotoxicity medium. CLL PBMC were suspended in PBS+0.1% BSA at 1×10⁶ cells/mL. The fluorescent dye carboxyfluorescein diacetate succinimidyl ester (CFSE) (Life Technologies, Carlsbad, Calif.) was added to this cell suspension at a concentration of 1 M. The cells were incubated 10 minutes at 37° C. After the incubation, the labeling reaction was stopped by adding a volume of FBS that was equal to the volume of cell suspension, and the cells were incubated for two minutes at room temperature. The cells were then washed and suspended in cytotoxcity medium.

Approximately 50,000 CD19-expressing CLL PBMC and 50,000 CCRF-CEM cells were combined in the same tubes with different numbers of CAR-transduced T-cells. In all experiments, the cytotoxicity of effector T-cells that were transduced with the FMC63-CD828Z CAR was compared to the cytotoxicity of negative control effector T-cells from the same subject that were transduced with the SP6-28Z control CAR or were not transduced. Co-cultures were established in sterile 5 mL test tubes (BD Biosciences, Franklin Lakes, N.J.) in duplicate at the following T-cell: target cell ratios: 20:1, 6.7:1, 2.2, and 0.7:1. The cultures were incubated for four hours at 37° C. Immediately after the incubation, 7-amino-actinomycin D (7AAD; BD Biosciences, Franklin Lakes, N.J.) was added as recommended by the manufacturer and flow cytometry acquisition was performed with a BD FacsCanto II (BD Biosciences). Analysis was performed with FlowJo Software (Treestar, Inc. Ashland, Oreg.). Analysis was gated on 7AAD-negative (live) cells, and the percentages of live CLL target cells and live CCRF-CEM negative control cells were determined for each T-cell plus target cell culture.

For each culture, the percent survival of CLL PBMC was determined by dividing the percent live CLL PBMC by the percent live CCRF-CEM negative control cells. The corrected percent survival of CLL PBMC was calculated by dividing the percent survival of CLL PBMC in each T-cell plus target cell culture by the ratio of the percent CLL target cells:percent CCRF-CEM negative-control cells in tubes containing only CLL target cells and CCRF-CEM negative control cells without any effector T-cells. This correction was necessary to account for variation in the starting cell numbers and for spontaneous target cell death. Cytotoxicity was calculated as the percent cytotoxicity of CLL PBMC=100-corrected percent survival of CLL PBMC. For all effector:target ratios, the cytotoxicity was determined in duplicate and the results were averaged.

The results of the cytotoxicity assay are shown in FIG. 8, and demonstrate that an inventive anti-CD19 CAR can be used in a method of destroying malignant B-cells.

Example 5

This example demonstrates that T-cells expressing an inventive anti-CD19 CAR can reduce malignant B-cell tumor growth in an animal model.

Immunocompromised NSG mice were injected subcutaneously with 4 million CD19+ NALM6 tumor cells. Six days later, after palpable tumors had formed, the mice were treated with a single intravenous injection of human T-cells that had been transduced with either a MSGV-FMC63-28Z CAR vector (described in Kochenderfer et al., *Journal of Immunotherapy,* 32(7): 689-702 (2009)) or the LSIN-47G4-CD8CD28Z CAR vector (described in Example 1). Tumors were measured every three days and compared to tumors in untreated mice.

The results of this experiment, shown in FIG. 9, indicate that T-cells expressing either the FMC63-28Z CAR or the 47G4-CD8CD28Z CAR markedly reduced tumor size in treated mice.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating or preventing a B-cell malignancy in a subject,
the method comprising administering to the subject an effective amount of one or more T cells or NK cells comprising a vector,
wherein the vector comprises a nucleic acid encoding a chimeric antigen receptor (CAR) directed against CD19, wherein the CAR comprises an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13, and
wherein the B-cell malignancy is leukemia, lymphoma, or multiple myeloma.

2. The method of claim 1, wherein the CAR comprises an amino acid sequence of SEQ ID NO: 10.

3. The method of claim 1, wherein the B-cell malignancy is multiple myeloma.

4. The method of claim 1, wherein the B-cell malignancy is leukemia.

5. The method of claim 4, wherein the leukemia is chronic lymphocytic leukemia.

6. The method of claim 1, wherein the B-cell malignancy is lymphoma.

7. The method of claim 6, wherein the lymphoma is follicular lymphoma, mantle-cell lymphoma, Burkitt lymphoma, diffuse large B-cell lymphoma, Hodgkin lymphoma, lymphoplasmacytic lymphoma, or marginal-zone lymphoma.

8. The method of claim 1, wherein the method comprises administering to the subject an effective amount of the one or more T cells comprising the vector.

9. The method of claim 1, wherein the method comprises administering to the subject an effective amount of the one or more NK cells comprising the vector.

10. The method of claim 1, wherein the method is a method of treating a B-cell malignancy in a subject.

11. The method of claim 10, wherein the CAR comprises an amino acid sequence of SEQ ID NO: 10.

12. The method of claim 10, wherein the B-cell malignancy is multiple myeloma.

13. The method of claim 10, wherein the B-cell malignancy is leukemia.

14. The method of claim 10, wherein the B-cell malignancy is lymphoma.

15. The method of claim 11, wherein the B-cell malignancy is multiple myeloma and wherein the method comprises administering to the subject an effective amount of the one or more T cells comprising the vector.

16. The method of claim 11, wherein the B-cell malignancy is leukemia and wherein the method comprises administering to the subject an effective amount of the one or more T cells comprising the vector.

17. The method of claim 11, wherein the B-cell malignancy is lymphoma and wherein the method comprises administering to the subject an effective amount of the one or more T cells comprising the vector.

18. The method of claim 11, wherein the B-cell malignancy is multiple myeloma and wherein the method comprises administering to the subject an effective amount of the one or more NK cells comprising the vector.

19. The method of claim 11, wherein the B-cell malignancy is leukemia and wherein the method comprises administering to the subject an effective amount of the one or more NK cells comprising the vector.

20. The method of claim 11, wherein the B-cell malignancy is lymphoma and wherein the method comprises administering to the subject an effective amount of the one or more NK cells comprising the vector.

* * * * *